US010301271B2

(12) United States Patent
Wu et al.

(10) Patent No.: US 10,301,271 B2
(45) Date of Patent: *May 28, 2019

(54) CRYSTALLINE FORMS OF TYROSINE KINASE INHIBITORS AND THEIR SALTS

(71) Applicant: PURDUE PHARMA L.P., Stamford, CT (US)

(72) Inventors: Jay Jie-Qiang Wu, Fremont, CA (US); Ling Wang, Fremont, CA (US)

(73) Assignee: Purdue Pharma L.P., Stamford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/511,946

(22) PCT Filed: Sep. 2, 2015

(86) PCT No.: PCT/US2015/048123
§ 371 (c)(1),
(2) Date: Mar. 16, 2017

(87) PCT Pub. No.: WO2016/043975
PCT Pub. Date: Mar. 24, 2016

(65) Prior Publication Data
US 2017/0313666 A1 Nov. 2, 2017

Related U.S. Application Data

(60) Provisional application No. 62/051,698, filed on Sep. 17, 2014.

(51) Int. Cl.
C07D 261/20 (2006.01)
A61P 29/00 (2006.01)
A61K 9/20 (2006.01)
A61K 31/496 (2006.01)

(52) U.S. Cl.
CPC .............. C07D 261/20 (2013.01); A61K 9/20 (2013.01); A61K 31/496 (2013.01); A61P 29/00 (2018.01); C07B 2200/13 (2013.01); Y02A 50/414 (2018.01)

(58) Field of Classification Search
CPC .................................................... C07D 261/20
See application file for complete search history.

(56) References Cited

U.S. PATENT DOCUMENTS

| 3,609,152 | A | 9/1971 | Hess et al. |
| 4,337,341 | A | 6/1982 | Zimmerman |
| 5,112,598 | A | 5/1992 | Biesalski |
| 5,556,611 | A | 9/1996 | Biesalski |
| 5,698,155 | A | 12/1997 | Grosswald et al. |
| 5,998,463 | A | 12/1999 | Hulin et al. |
| 7,252,822 | B2 | 8/2007 | Shelton et al. |
| 7,425,329 | B2 | 9/2008 | Shelton et al. |
| 7,671,077 | B2 | 3/2010 | Lin |
| 7,718,674 | B2* | 5/2010 | Aberg .................. C07D 211/26 514/318 |
| 8,669,265 | B2 | 3/2014 | Reddy et al. |
| 8,809,530 | B1 | 8/2014 | Wu et al. |
| 8,999,992 | B2* | 4/2015 | Wu ....................... C07D 261/20 514/254.04 |
| 9,040,508 | B2 | 5/2015 | Wu et al. |
| 9,388,146 | B2* | 7/2016 | Wu ....................... C07D 261/20 |
| 9,718,794 | B2 | 8/2017 | Wu et al. |
| 9,738,659 | B2 | 8/2017 | Wu et al. |
| 9,993,473 | B2 | 6/2018 | Wu et al. |
| 10,124,002 | B2 | 11/2018 | Wu et al. |
| 2001/0051622 | A1 | 12/2001 | Rosenzweig-Lipson et al. |
| 2004/0071701 | A1 | 4/2004 | Delafoy et al. |
| 2004/0131615 | A1 | 7/2004 | Shelton et al. |
| 2005/0054651 | A1 | 3/2005 | Natarajan et al. |
| 2006/0257337 | A1 | 11/2006 | Sherris |
| 2008/0113974 | A1 | 5/2008 | Hurtevent et al. |
| 2008/0161292 | A1 | 7/2008 | Giranda et al. |
| 2011/0160240 | A1 | 6/2011 | Ryckman et al. |
| 2011/0301133 | A1 | 12/2011 | Wu et al. |
| 2012/0003184 | A1 | 1/2012 | Garcia Gonzalez et al. |
| 2013/0158264 | A1 | 6/2013 | Castelhano et al. |
| 2014/0228331 | A1 | 8/2014 | Wu et al. |
| 2014/0275113 | A1 | 9/2014 | Wu et al. |
| 2015/0174124 | A1 | 6/2015 | Wu et al. |
| 2016/0002182 | A1 | 1/2016 | Wu et al. |
| 2017/0105990 | A1 | 4/2017 | Wu et al. |
| 2018/0057469 | A1 | 3/2018 | Wu et al. |

FOREIGN PATENT DOCUMENTS

| CN | 101223175 A | 7/2008 |
| CN | 102292338 A | 12/2011 |
| JP | 2006-523714 A | 10/2006 |
| JP | 2007-503392 A | 2/2007 |
| JP | 2007-291079 A | 11/2007 |
| KR | 2003-0095729 A | 12/2003 |
| RU | 2065438 C1 | 8/1996 |
| WO | WO 99/10341 A1 | 3/1999 |
| WO | WO 00/75139 A2 | 12/2000 |
| WO | WO 03/027111 A1 | 4/2003 |
| WO | WO 2004/071486 A1 | 8/2004 |
| WO | WO 2004/094452 A2 | 11/2004 |
| WO | WO 2005/020897 A2 | 3/2005 |
| WO | WO 2006/007864 A1 | 1/2006 |

(Continued)

OTHER PUBLICATIONS

McCarthy et al. Expert opin.Ther.Patents 24(7), pp. 731-744 (2014).*
Zhang et al.Nature Reviews, vol. 9, pp. 28-39 (2009).*
Stachel et al. J.Med.Chem.vol. 57,pp. 5800-5816 (2014).*
Akers, Michael J., Chapter 41 of Remington the Science and Practice of Pharmacy, 21st Edition, (David B. Troy ed., Lippincott Williams & Wilkins), pp. 802-836. (Year: 2005).*
Noriaki Hirayama, *Yuki Kagoubutu Kessho Sakusei Handbook* (Handbook for Preparing Crystal of Organic Compound), pp. 10-11, 57-72, and 78-91, Maruzen Co., Ltd., Japan (2008).

(Continued)

Primary Examiner — Emily A Bernhardt
(74) Attorney, Agent, or Firm — Sterne, Kessler, Goldstein & Fox P.L.L.C.

(57) ABSTRACT

The disclosure relates to various polymorphic forms and amorphous form of sodium 4-((3-(4-cyclohexylpiperazin-1-yl)-6-oxo-6H-anthra[1,9-cd]isoxazol-5-yl)amino)benzoate, including the polymorphic form A, mixtures of the polymorphs, process for the preparation thereof and the use thereof in a pharmaceutical composition containing thereof.

25 Claims, 17 Drawing Sheets

(56) References Cited

FOREIGN PATENT DOCUMENTS

| WO | WO 2006/078711 A2 | 7/2006 |
|---|---|---|
| WO | WO 2006/079720 A1 | 8/2006 |
| WO | WO 2007/133249 A2 | 11/2007 |
| WO | WO 2008/021463 A2 | 2/2008 |
| WO | WO 2008/053863 A1 | 5/2008 |
| WO | WO 2009/067197 A2 | 5/2009 |
| WO | WO 2010/077680 A2 | 7/2010 |
| WO | WO 2012/097000 A1 | 7/2012 |
| WO | WO 2012/119079 A1 | 9/2012 |
| WO | WO 2014/152663 A1 | 9/2014 |

OTHER PUBLICATIONS

The English translation of the Office Action mailed in Japanese Patent Application No. 2016-502487, dated Jan. 29, 2018.
Office Action dated Feb. 8, 2018, in U.S. Appl. No. 15/648,527, Wu et al., filed Jul. 13, 2017.
Food and Drug Administration, "Guidance for Industry. Estimating the Maximum Safe Starting Dose in Initial Clinical Trials for Therapeutics in Adult Healthy Volunteers," in *Pharmacology and Toxicology*, pp. 1-27, USFDA, United States (2005).
International Search Report in International Application No. PCT/US2009/067197, Korean Intellectual Property Office, Republic of Korea, dated Aug. 18, 2010, 4 pages.
European Office Action, Invitation pursuant to Rule 63(1) EPC, in EP Application No. 09836726.1, dated May 25, 2012, 5 pages.
Written Opinion of the International Searching Authority in International Application No. PCT/US2009/067197, Korean Intellectual Property Office, Daejeon, Republic of Korea, dated Aug. 18, 2010, 5 pages.
Aurora Fine Chemicals, "Chemical Catalog Online," aurorafinechemicals.com, accessed at http://online.aurorafinechemicals.com, accessed on Mar. 28, 2013, 1 page.
Bach, T., et al., "Enantioselective [6π]-Photocyclization Reaction of an Acrylanilide Mediated by a Chiral Host. Interplay between Enantioselective Ring Closure and Enantioselective Protonation," *J. Org. Chem.* 68(3):1107-1116, American Chemical Society, United States (2003).
Beelitz, K., et al., "Pyrido[2,3-d]thieno[3,2-b][6H]thiopyran—a New Heterocyclic Ring System," *Z. Naturforsch.* 34b:1573-1575, De Gruyter, Germany (1979).
Aurora Fine Chemicals, "Benzoic Acid, 4- [[3-(4-cyclohexyl-1-piperazinyl)-6-oxo-6H-anthra[1,9-cd]isoxazol-5-yl]amino]," CAS Registry No. 892242-64-7, STN Entry Date Jul. 12, 2006.
Chicharro, R., et al., "Synthesis of Tri- and Tetracyclic Condensed Quinoxalin-2-ones Fused Across the C-3—N-4 Bond," *Eur. J. Org. Chem.* 12:2314-2326, Wiley-VCH Verlag GmbH & Co. KGaA, Weinheim, Germany (2003).
Doddareddy, M.R., et al., "3D pharmacophore based virtual screening of T-type calcium channel blockers," *Bioorg. Med. Chem.* 15(2):1091-1105, Elsevier Ltd., England (2006).
Fraser, R.R., et al., "Experimental and Theoretical Studies of Acid-Catalyzed $^{18}O$ Exchange Rates of Conformationally Rigid Ketones. Is the Antiperiplanar Effect Important?" *J. Org. Chem.* 58(16):4431-4440, American Chemical Society, United States (1993).
Gopalan, B., et al., "Studies in Claisen Rearrangement: Novel Thermal Transformation of α-Aryloxymethylacrylic Acids and their Derivatives," *Tetrahedron* 41(15):3153-3159, Pergamon Press Ltd., England (1985).
Gornostaev, L.M., et al.,"Amination of Anthra[1,9-c,d]Isoxazol-6-ones," *Chemistry of Heterocyclic Compounds* 16(7):704-707, Plenum Publishing Corporation, United States (1980), translated from *Khimiya Geterotsiklicheskikh Soedinenii* 7:912-915 (1980).
Ito, N., et al., "A medium-term rat liver bioassay for rapid in vivo detection of carcinogenic potential of chemicals," *Cancer Science* 94:3-8, Wiley Publishing on behalf of the Japanese Cancer Association, England (2003).
Kim, B.S. and Kim, K., "A Facile and Convenient Synthesis of 3-Alkylamino-5-arylthiophenes with a Variety of Substituents at C-2 and Studies of Reaction Mechanisms," *J. Org. Chem.* 65:3690-3699, American Chemical Society, United States (2000).
Krishnamoorthy, T.V., et al., "Trifluoroacetic Acid Catalyzed and Thermal Rearrangement of α-Aryloxymethyl Cinnamic Acids," *Tetrahedron Letters* 26(14):1747-1748, Pergamon Press Ltd., England (1985).
Kurasawa, Y., et al., "Synthesis and Reactions of 3-(1,2,4-Triazol-5-yl)methylene-2-oxo-1,2,3,4-tetrahydroquinoxalines," *Chem. Pharm. Bull.* 32 (12):4752-4757 , Pharmaceutical Society of Japan, Japan (1984).
Link, A. and Kunick, C., "d-Fused [1]Benzazepines with Selective in Vitro Antitumor Activity: Synthesis and Structure-Activity Relationships," *J. Med. Chem.* 41(8):1299-1305, American Chemical Society, United States (1998).
Patil, S., et al., "Synthesis and biological evaluation of novel 5(H)-phenanthridin-6-ones, 5(H)-phenanthridin-6-one diketo acid, and polycyclic aromatic diketo acid analogs as new HIV-1 integrase inhibitors," *Bioorg. Med. Chem.* 15(3):1212-1228, Elsevier Science, England (2007).
Supplementary Partial European Search Report in EP Application No. 09836726.1, dated Oct. 1, 2012, 18 pages.
Young, S.M., et al., "Duplex High-Throughput Flow Cytometry Screen Identifies Two Novel Formylpeptide Receptor Family Probes," *Cytometry A* 75(3):253-263, Wiley-Liss, United States (2009) (available online Sep. 2008).
Yunosova, O.N., et al., "Selective alkylamination of 3,5-dihalo-6H-anthra[1,9-c,d]isoxazol-6-ones," *Invest. Vys. Uceb. Zaved. Himia I Himi. Technol.* 47(8):124-127, Wiley-VCH Verlag GmbH & Co. KGaA, Weinheim, Germany (2004).
Raychaudhuri, S.K. and Raychaudhuri, S.P., "NGF and Its Receptor System: A New Dimension in the Pathogenesis of Psoriasis and Psoriatic Arthritis," *Contemporary Challenges in Autoimmunity*; Ann. N.Y. Acad. Sci. 1173: 470-477, New York Academy of Sciences, United States (2009).
Declercq, S.D. and Pouliot, R., "Promising New Treatments for Psoriasis," *The Scientific World Journal* 2013:1-9, Hindawi Publishing Corporation, United States (Jul. 2013).
Frossard, N., et al., "Nerve growth factor and its receptors in asthma and inflammation," *European Journal of Pharmacology* 500:453-465, Elsevier B.V., Netherlands (2004).
De Melo-Jorge, M. and Pereira Perrin, M., "The Chagas' Disease Parasite *Trypanosoma cruzi* Exploits Nerve Growth Factor Receptor TrkA to Infect Mammalian Hosts," *Cell Host & Microbe* 1:251-261, Elsevier Science, United States (2007).
Guerios, S.D., et al., "Blockade of NGF and trk receptors inhibits increased peripheral mechanical sensitivity accompanying cystitis in rats," *Am. J. Physiol. Regul. Integr. Comp. Physiol.* 295:R111-R122, American Physiological Society, United States (2008).
International Search Report and Written Opinion of the International Searching Authority in International Application No. PCT/US2014/027591, Korean Intellectual Property Office, Daejeon Metropolitan City, Republic of Korea, dated Aug. 29, 2014, 11 pages.
Wang, F., et al., "Design, synthesis, biochemical studies, cellular characterization, and structure-based computational studies of small molecules targeting the urokinase receptor," *Bioorg. Med. Chem.* 20:4760-4773, Elsevier Science, England (2012).
McCarthy, C. and Walker, E., "Tropomyosin receptor kinase inhibitors: a patent update 2009-2013," *Expert Opin. Ther. Patents* 24(7):731-744, Informa UK, Ltd., England (Jul. 2014).
Zhang, J., et al., "Targeting cancer with small molecule kinase inhibitors," *Nature Reviews Cancer* 9:28-39, Nature Publishing Group, England (2009).
Stachel, S.J., et al., "Maximizing Diversity from a Kinase Screen: Identification of Novel and Selective pan-Trk Inhibitors for Chronic Pain," *J. Med. Chem.* 57:5800-5816, American Chemical Society, United States (Jun. 2014).
Berge, S.M., et al., "Pharmaceutical Salts," *J. of Pharmaceutical Sciences* 66:1-19, American Pharmaceutical Assn., United States (1977).

(56) References Cited

OTHER PUBLICATIONS

Hancock, B.C. and Parks, M., "What is the true solubility advantage for amorphous pharmaceuticals?" *Pharm. Res.* 17(4):397-404, Kluwer Academic/Plenum Publishers, United States (2000).
Bennett, G.J. and Xie, Y.-K., "A peripheral mononeuropathy in rat that produces disorders of pain sensation like those seen in man," *Pain* 33(1):87-107, Elsevier Science Publishers B.V., Netherlands (1988).
Calcutt, N.A., "Experimental models of painful diabetic neuropathy," *J. Neurol. Sci.* 220(1-2):137-139, Elsevier B.V., Netherlands (2004).
Kim, S.H. and Chung, J.M., "An experimental model for peripheral neuropathy produced by segmental spinal nerve ligation in the rat," *Pain* 50(3):355-363, Elsevier Science Publishers B.V., Netherlands (1992).
Lynch, J.J., III et al, "An adenosine kinase inhibitor attenuates tactile allodynia in a rat model of diabetic neuropathic pain," *Eur. J. Pharmacol.* 364(2-3):141-146, Elsevier Science B.V., Netherlands (1999).
Office Action dated Jul. 16, 2014 in U.S. Appl. No. 14/208,244, Wu, et al., filed Mar. 13, 2014.
Office Action dated Sep. 8, 2014 in U.S. Appl. No. 14/208,244, Wu, et al., filed Mar. 13, 2014.
Notice of Allowance dated Dec. 3, 2014 in U.S. Appl. No. 14/208,244, Wu, et al., filed Mar. 13, 2014.
Office Action dated Apr. 24, 2015 in U.S. Appl. No. 14/635,635, Wu, et al., filed Mar. 2, 2015.
English language Abstract of Japanese Patent Publication No. JP 2007-291079 A, Espacenet database—Worldwide, European Patent Office (listed as document FP2 on the accompanying form PTO/SB/08A) (2008).
English language Abstract of Korean Patent Publication No. KR 2003-0095729 A, Espacenet database—Worldwide, European Patent Office (listed as document FP4 on the accompanying form PTO/SB/08A) (2003).
Office Action dated Nov. 13, 2015 in U.S. Appl. No. 14/635,635, Wu, et al., filed Mar. 2, 2015.
Office Action dated Nov. 2, 2016 in U.S. Appl. No. 14/772,264, Wu, et al., § 371(c) date Dec. 28, 2015.
Extended European Search Report for EP Application No. 14770743.4, Munich, Germany, dated Sep. 14, 2016, 5 pages.
International Search Report and Written Opinion for International Application No. PCT/US2015/048123, ISA/US, Commissioner for Patents, United States Patent and Trademark Office, dated Dec. 4, 2015, 11 pages.
Notice of Allowance dated Mar. 4, 2016 in U.S. Appl. No. 14/635,635, Wu, et al., filed Mar. 2, 2015.
Grodowska, K. and Parczewski, A., "Organic solvents in the pharmaceutical industry," *Acta poloniae pharmaceutica* 67(1):3-12, Polish Pharmaceutical Society, Poland (2010).
Partial Translation (pp. 124-126) of Yunosova, O.N., et al., "Selective alkylamination of 3,5-dihalo-6H -anthrar[1,9-c,d]isoxazol-6-ones," *Izvest. Vys. Uceb. Zaved. Himia I Himi. Technol.* 47(8):124-127, Wiley-VCH Verlag GmbH & Co. KGaA, Weinheim, Germany (2004), USPTO, Alexandria, VA (Aug. 4, 2016).
U.S. Food and Drug Administration, "Dosage Form," CDER Data Element No. C-DRG-00201, CDER Approved Date Apr. 14, 1992, last updated Jan. 30, 2009, accessed at http://www.fda.gov/Drugs/DevelopmentApprovalProcess/FormsSubmissionRequirements/ElectronicSubmissions/DataStandardsManualmonographs/ucm071666.htm, accessed on Aug. 8, 2016, 21 pages.
Notice of Allowance dated Mar. 22, 2017 in U.S. Appl. No. 14/772,264, Wu, et al., § 371(c) date Dec. 28, 2015.
Raychaudhuri, S.P., et al., "K252a, a High-Affinity Nerve Growth Factor Receptor Blocker, Improves Psoriasis: An In Vivo Study Using the Severe Combined Immunodeficient Mouse-Human Skin Model," *J. Invest. Dermatol.* 122:812-819, The Society for Investigative Dermatology, Inc., United States (2004).
Office Action dated Jul. 14, 2017 in U.S. Appl. No. 15/185,754, Wu, et al., filed Jun. 17, 2016.
Notice of Allowance dated Dec. 28, 2017 in U.S. Appl. No. 15/185,754, Wu, et al., filed Jun. 17, 2016.
Notice of Allowance dated Jul. 12, 2018, in U.S. Appl. No. 15/648,527, Wu et al., filed Jul. 13, 2017.

\* cited by examiner

CRYSTALLINE FORMS OF TYROSINE KINASE INHIBITORS AND THEIR SALTS

CROSS REFERENCE TO RELATED APPLICATIONS

This Application is a PCT International Patent Application, which claims the benefit of priority to U.S. Provisional Application No. 62/051,698, filed on Sep. 17, 2014, the entire contents of which are hereby incorporated by reference in their entirety for all purposes.

FIELD OF THE DISCLOSURE

The invention relates to a novel composition and polymorphs of sodium 4-((3-(4-cyclohexylpiperazin-1-yl)-6-oxo-6171-anthra[1,9-cd]isoxazol-5-yl)amino)benzoate, particularly the polymorphic form A, mixtures of the polymorphs process for the preparation thereof and the use thereof in a pharmaceutical composition containing thereof.

BACKGROUND

Trk family proteins are receptor tyrosine kinases composed of three family members, TrkA, TrkB and TrkC. They bind with high affinity to, and mediate the signal transduction induced by the Neurotrophin family of ligands whose prototype members are Nerve Growth Factor (NGF), Brain-Derived Neurotrophic Factor (BDNF) and Neurotrophin 3-5 (NT 3-5). In addition, a co-receptor lacking enzymatic activity, p75, has been identified which binds all neurotrophines (NTs) with low affinity and regulates neurotrophin signaling. A critical role of the irks and their ligands during the development of the central and peripheral nervous systems have been established through gene disruption studies in mice. In particular, TrkA-NGF interaction was shown as a requirement for the survival of certain peripheral neuron populations involved in mediating pain signaling. It has been shown that increased expression of TrkA also correlates with an increased level of pain in the case of pancreatic cancer (Zhu, et al, *Journal of clinical oncology*, 17:2419-2428 (1999)). Increased expression of NGF and TrkA was also observed in human osteoarthritis chondrocytes (Iannone et al, *Rheumatology* 41:1413-1418 (2002)).

TrkA (Troponyosin-receptor kinase A) is a cell surface receptor kinase containing an extracellular, a transmembrane, and a cytoplasmic kinase domain. The binding of a neurotrophin triggers oligomerization of the receptors, phosphorylation of tyrosine residues in the kinase domain, and activation of intercellular signaling pathways, including Ras/MAPK cascade, PI3K/AKT, and IP3-dependent Ca2+ release. Tyrosine kinase activity is an absolute requirement for signal transduction through this class of receptor. NGF receptors have been also found on a variety of cell types outside of the nervous system. For example, TrkA has been also found on human monocytes, T- and B-lymphocytes and mast cells.

There are several examples of either anti-TrkA antibodies or anti-NGF antibodies known in the art. For examples, PCT Publication Nos. WO 2006/131952, WO 2005/061540 and EP 1181318 disclose use of anti-TrkA antibodies as effective analgesics in in-vivo animal models of inflammatory and neuropathic pain. PCT Application Nos. WO 01/78698, WO 2004/058184 and WO 2005/019266 disclose the use of an NGF antagonist for preventing or treating pain. PCT Application WO 2004/096122 describes a method for the treatment or the prevention of pain with co-administration of an anti-NGF antibody and an opioid analgesic. PCT Application WO 2006/137106 discloses a method for the treatment or the prevention of pain with co-administration of an anti-TrkA antibody and an opioid analgesic. In addition, profound or significantly attenuated reduction of bone pain caused by prostate cancer metastasis has been achieved by utilization of an anti-NGF antibody (Sevik, M A. et al, *Pain* 115:128-141 (2005)).

Loss-of-function mutations in TrkA (NTRK1) lead to congenital insensitivity to pain with anhidrosis [*Nat Genet* 1996; 13:485-8] and the anti-NGF antibody tanezumab has demonstrated clinical efficacy in osteoarthritis pain and diabetic neuropathic pain [*N Engl J Med* 2010; 363:1521-31: *Arthritis Rheum* 2013; 65:1795-803]. Additionally, Trk inhibitors show excellent efficacy in preclinical models of pain [*Mol Pain* 2010; 6:87-100]. Array has recently demonstrated equivalent efficacy with allosteric TrkA-selective inhibitors in pain models, which have the potential to be safer than pan-Trk inhibitors as discussed later [*Array Website*, 2012. Available from: http://www.arraybiopharma.conm/_documents/Pubbcation/PubAttachment587.pdf [*Last accessed* 22 Jan. 2014]. There is some evidence that inhibition of Trks may be beneficial in the treatment of Alzheimer's disease. NGF and TrkA levels are elevated in airways of asthmatics (asthma) [*J Asthma* 2013; 50:712-17; *Respirology* (2009) 14, 60-68; and *PLoS ONE* 4(7): e6444. doi:10.1371/journal.pone.0006444] and may contribute to inflammation, hyperresponsiveness and remodeling. NGF and TrkA has also been shown to exacerbate ovalbumin-induced airway inflammation in rodents [*Exp Ther Med* 2013; 6:1251-8]. CT327 is a topical TrkA inhibitor that has been clinically evaluated by Creabilis for chronic pruritus in diseases such as atopic dermatitis, psoriasis and itch [http://clinicaltrials.gov/show/NCT1808157]. Inhibition of TrkA may have utility in the treatment of Chagas disease. *Trypanosoma cruzi*, the agent of Chagas' disease, utilizes Trk to invade various cell types in the human host [*Infect Immun* 2009; 77: 1368-75; *Infect Immun* 2011; 79:4081-7].

Selective inhibition of TrkA kinase activity may also have utility in the treatment of ear diseases [*Laryngoscope* 2011 October; 121(10):2199-213], liver cirrhosis and hepatocellular carcinoma [*World J Gastroenterol* 2007 Oct. 7; 13(37): 4986-4995], Pulmonary Inflammatory Diseases [*Immunology and Microbiology>>"Inflammatory Diseases—A Modern Perspective"*, book edited by Anit Nagal, ISBN 978-953-307-444-3, Published: Dec. 16, 2011, Chapter 5: *Expression and Role of the TrkA Receptor in Pulmonary Inflammatory Diseases*], fibrosis [*J Cell Commun Signal.* March 2010; 4(1): 15-23. Patent Application: PCT/GB2004/004795], Pterygium [*Int. J. Exp. Path.* (2009), 90, 615-620], lung diseases [*Expert Rev Respir Med.* 2010 June; 4(3): 395-411.], pulmonary sarcoidosis [Dagnell et al. *Respiratory Research* 2010, 11:156], bladder dysfunction [*Neurourology and Urodynamics* 30:1227-1241 (2011); *BJU International* 111, 372-380; *J Urol.* 2013 August; 190(2): 757-764; *Neurourology and Urodynamics* 33:39-45 (2014)], lower urinary tract dysfunction [*International Journal of Urology* (2013) 20, 13-20], Paget's disease [*J Cutan Pathol* 2010; 37: 1150-1154], diabetic nephropathy [*Diabetes*. September 2012, Vol. 61 Issue 9, p 2280-2288; *Regulatory Peptides* 135 (2006) 30-38.], irritable bowel syndrome [*Neurogastroenterol Motil* (2013) 25, e740-e754], radiation protection [*Radiother Oncol.* 2012 June; 103(3): 380-387.].

Furthermore, pain, which can be caused by the disease itself or by treatments, is common in people with cancer, although not all people with cancer will experience pain. Approximately 30% to 50% of people with cancer experience pain while undergoing treatment, and 70% to 90% of people with advanced cancer experience pain [Lesage P. and Portenoy R K. *Cancer Control; Journal of the Moffitt Cancer Center* 1999; 6(2):136-145]. Cancer pain is a complex, temporally changing symptom which is the end result of mixed mechanism pain. It involves inflammatory, neuropathic, ischemic, and compression mechanisms at multiple sites [*Pathophysiology of cancer pain and opioid tolerance. In: The British Pain Society's Cancer Pain Management. The British Pain Society website. www.britishpainsociety.org. Published January* 2010. Accessed Jan. 29, 2013]. It is a subjective, heterogeneous experience that is modified by individual genetics, past history, mood, expectation, and culture. Cancer pain syndromes are categorized as acute and chronic based on onset and duration. Acute pain syndromes have a sudden, well-defined onset, an identifiable cause (e.g. surgery), subject to sympathetic output (fight or flight response), and are expected to improve with management. Chronic pain on the other hand, has a less distinct onset, has a prolonged and fluctuating course, and is largely driven by central sensitization and neuroplastic responses from acute injury [Fornasari D. *Pain mechanisms in patients with chronic pain. Clin Drug Investig* 201; 32(suppl 1):45-52; Latremoliere A, Woolf C J. *Central sensitization: a generator of pain hypersensitivity by central neural plasticity. J Pain* 2009; 10:895-926]. It is often characterized by "pain flares" referred to as breakthrough pain [Portenoy R K, Dhingra L K. *Assessment of cancer pain. In: Drews R E*, ed. UpToDate. Waltham, Mass.: UpToDate; 2013].

The therapeutic implications of an effective Trk inhibitor may well go beyond pain therapy. A TrkA polymorphism has been identified to be associated with schizophrenia [*J Psychiatr Res.* 2009 October; 43(15):1195-9]. The subversion of this receptor and its signaling pathway in certain malignancies has also been documented. The potential utility of Trk inhibitors in oncology has been covered previously (for reviews, see, *Expert Opin Ther Pat.* 2014 July; 24(7):731-44; *Nat Rev Cancer,* 2004; 4:361-70; *Clin Cancer Res,* 2009; 15:5962-7). TrkA and/or Trk(B/C) have been implicated in the survival and metastasis of prostate [*Expert Opin Investig Drugs,* 2007; 16:303-9; Prostate, 2000; 45:140-8], breast [*Cytokine Growth Factor Rev,* 2012; 23:357-65], hepatocellular carcinoma (liver cancer) and liver cirrhosis [*World J Gastroenterol.* 2007 Oct. 7; 13(37):4986-95; *Gastroenterology.* 2002 June; 122(7):1978-86; *Biochem Biophys Res Commun.* 2011 Mar. 4; 406(1):89-95; *Digestive Diseases and Sciences, Vol.* 55, No. 10, (October 2010), pp. 2744-55, ISSN 0163-2116], intrahepatic cholangiocarcinoma [*World J Gastroenterol* 2014 April 14; 20(14): 4076-4084], liver fibrosis [*Expert Rev Mol Med.;* 11: e7. doi: 10.1017/S1462399409000994], ovarian cancer [*Gynecol Oncol.* 2007 January; 104(1):168-75], pancreatic cancers [*Clin Cancer Res.,* 2005; 11:440-9], oral cancer [*Dermatol Surg* 2004; 30:1009-1016] and oral cancer pain [*J Dent Res* 91(5):447-453, 2012], skin cancer [*Am J Clin Pathol* 2004; 122:412-420], cervical cancer [*African Journal of Biotechnology Vol.* 10(38), pp. 7503-7509, 25 Jul., 2011], bone cancer [*J Vet Intern Med* 2008; 22:1181-1188]. Other rare cancers such as congenital mesoblastic nephroma, infant fibrosarcoma [*Am J Pathol,* 1998; 153:1451-8] and secretory breast carcinoma [*Cancer Cell,* 2002; 347-8] carry Tel-TrkC gene rearrangements. Somatic rearrangements of TrkA have been detected in a small but consistent subset of papillary thyroid rumors [*Cancer Lett* 2006; 232:90-8; *Mol Cell Endocrinol* 2010; 321:44-9; *Genomics.* 1995 Jul. 1; 28(1): 15-24; *Int J Cancer.* 1999 Mar. 15; 80(6):842-7].

An exciting new avenue in the field has recently opened with the discovery of oncogenic TrkA (NTRK1) rearrangements in a small subset of lung cancer patients [*Nat Med* 2013; 19:1469-72], and in colorectal cancer (as TPM3-TrkA funsion mutation) [*Mol Oncol.* 2014 Jun. 12. pii: S1574-7891(14)00125-2]. Tumor samples from 3 out of 91 lung cancer patients without previously identified genetic alterations demonstrated evidence of TrkA gene (NTRK1) fusions. These gene fusion mutations are intracellular oncogenic proteins, and they have constitutive activated intracellular TrkA kinase activity and transformed fibroblast cells. TrkA (NTRK1), TrkB (NTRK2), or TrkC (NTRK3) fusions have also been identified in glioblastoma, spitz tumors, spitzoid melanomas, acute myelogenous leukemia and secretory breast cancer [Greco A, et al. *Mol Cell Endocrinol* 2009; Alberti L, et al. *J Cell Physiol* 2003; Martin-Zanca D et al. *Nature* 1986; Wiesner T, et al. *Nat Commun* 2013; Vaishnavi A, et al, *Nat Med* 2013]. The identification of this gene rearrangement or fusion mutations may enable a patient stratification approach, similar to that utilized effectively by Pfizer, enabling the rapid registration and approval of crizotinib [*Drugs* 2013; 73:2031-51].

In fact, a patient with TrkA-positive metastatic colorectal cancer was recently clinically treated with RXDX-101, a pan Trk inhibitor and achieved a partial response [Ignyta, Inc. News Release. May 31, 2014. Website: http://finance.yahoo.cominews/ignyta-announces-interim-data-rxdx-190000889.html]. Our own search of public human cancer genomic databases uncovered that many types of human cancers have TrkA fusions or fusion mutations, for examples, breast cancer (e.g., CAL-51, CAMA-1 and other 3 human breast cancer cells from 5 patients), endometrial cancer (e.g., RK95-2 and other 7 human cancer cells from 8 patients), blood cancer (e.g., CML-T1 and other 3 cancer cells from 4 patients), liver cancer (SNU-878 and other 2 cancer cells from 3 patients), colorectal cancer (e.g., SNU-C4 and other 10 cancer cells from 11 patients), pancreatic cancer (e.g., pane 02.13 and panc 03.27 from 2 patients), and skin cancer (e.g., LOX IMVI and other 4 cancer cells from 5 patients), that a TrkA selective inhibitor like the ones disclosed in current invention or a compound of the present invention can be utilized to precisely inactive intracellular TrkA kinase activity in those constitutive activated intracellular oncogenic proteins, i.e., TrkA fusion mutations, and hence as an effective human cancer treatment therapy for the types of human cancers listed above.

The tyrosine kinase activity of Trk is believed to promote the unregulated activation of cell proliferation machinery. It is believed that inhibitors of TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies. Lestaurtinib (CEP-701, Cephalon), an indolocarbazole inhibitor of several tyrosine kinases, including Flt-3 and TrkA, and CEP-751, a pan Trk inhibitor have been entered Phase II clinical trails for the treatment of acute myelogenous leukaemia (AML), pancreatic cancer and multiple myeloma (MM) and/or prostate cancer.

Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. Overall, the oncogenic properties of Trk signaling in multiple tumor types makes the modulation of the Trk receptor signaling a potentially attractive therapeutic intervention point in different malignancies.

Besides antibodies, however, few TrkA inhibitors are known and very few (if any) show high TrkA kinase selectivity (including staurosporine derived TrkA inhibitors, CEP-751 and CEP-701). It has been rarely known in the art that a synthetic organic molecule or compound had been used as either direct sub-type selective TrkA or NGF inhibitor or antagonist for treatment or prevention of pain in particular. It may due mainly to the facts of difficulty in identifying potent and particularly sub-type selective anti-TrkA or anti-NGF small organic compounds, though the crystal structure of NGF in complex with the TrkA receptor has been determined (Nature 401:184-188 (1996) & 254:411 (1991)).

Due to the therapeutic promise associated with inhibiting TrkA, and the relative lack of potent and selective inhibitors, it is great need to discover the potent and particular isoform selective TrkA inhibitors, especially of orally active small synthetic molecules for possible treatment or prevention of the disease or disorders associated with TrkA activity.

The free acid of compound 4-((3-(4-cyclohexylpiperazin-1-yl)-6-oxo-6H-anthra[1,9-cd]isoxazol-5-yl)amino)benzoic acid ("Compound 701") and its pharmaceutical composition are known in US Patent Application No. 20110301133 A1 (corresponding PCT Patent Application, WO2009/067197, which is hereby incorporated by reference) and has the following chemical structure:

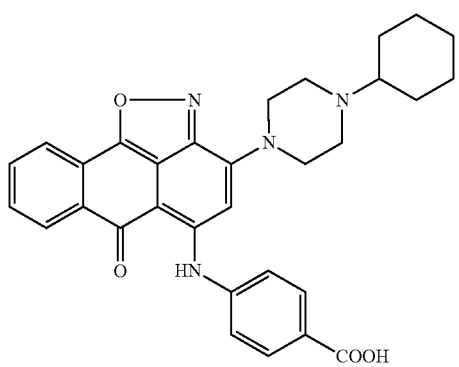

Compound 701, and the physiologically acceptable salts thereof, have valuable pharmacological properties. Compound 701 is a receptor tyrosine kinase inhibitor, particularly a potent NGF receptor TrkA inhibitor which, by virtue of its pharmacological properties, may be used, for examples, for the treatment and/or prevention of acute and chronic pain, cancer, restenosis, atherosclerosis, psoriasis, thrombosis, skin diseases, inflammation, inflammation related diseases, or a disease, disorder or injury relating to dysmyelination or demyelination. Other possible therapeutic applications can be found in WO2009/067197, the contents of which are hereby referred to.

Due to the limited solubility of the free acid Compound 701, it is very difficult to achieve practical oral bioavailability in the in-vivo systems, for example, in rat. Salt formation has been widely used in the art to improve lipophilic, water solubility and/or oral bioavailability, among other issues in the industry. However, it is problematic and huge challenge for selection and testing of the enormous numbers of possible salt forms in practice, since Compound 701 is zwitterionic molecule, there are vast amount of counterions and/or molecules that could form salts or co-crystals with Compound 701 and they can be from either (i) anionic counterions, for examples, acetate, benzoate, bicarbonate, bisulfite, norate, bromide, carbonate, chloride, citrate, formate, fumerate, glcuconate, glucuronate, hydrochloride, malate, nitrate, phosphate, salicylate, succinate and tartrate; (ii) cationic counter-ions, for examples, ammonium, piperazine, diethlyamine, diethanolamine, imidazole, diethylammonium, ethylenediamine, betaine, lithium, sodium, potassium, calcium, magnesium, aluminum, zinc, bismuth and stonium; or (iii) zwitterionic molecules, for examples, glycine, bicine, tricine, sulfamic acid, lysergic acid, and psilocybin. Furthermore, each salt or co-crystal forms may form various polymorphs with various degrees of physicochemical properties in terms of, for examples, solubility, stability, and oral bioavailability, it is therefore problematic and huge challenge in practice.

Another aspect which is important in drug development is that the active substance should have the most stable possible crystalline morphology for the pharmaceutical quality of a medicinal formulation. If this is not the case, the morphology of the active substance may change in certain circumstances under the conditions of manufacture of the preparation. Such a change may in turn affect the reproducibility of the manufacturing process and thus lead to final formulations which do not meet the high quality requirements imposed on pharmaceutical formulations. To this extent it should generally be borne in mind that any change to the solid state of a pharmaceutical composition which can improve its physical and chemical stability gives a significant advantage over less stable forms of the same drug.

SUMMARY OF THE DISCLOSURE

The present invention provides, among other things, small molecule compounds and their salts or solvates in various crystalline forms and amorphous form as NGF receptor TrkA inhibitor and/or antagonist for the preparation of a medicament for the treatment and/or prevention of diseases associated, directly or indirectly with modulation of activity or expression of TrkA protein kinase, which include pain (i.e. reducing pain for a subject in need thereof, including acute pain, chronic pain, inflammatory pain, neuropathic pain, cancer pain, and generalized pain disorder); certain cancers (e.g., pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas), atopic dermatitis, psoriasis, skin diseases, itch, liver fibrosis, liver cirrhosis, scabies, pityriasis, inflammatory bowel disease, inflammatory arthritis, asthma, human airway diseases. Chagas' disease, parasitic diseases, Alzheimer's, restenosis, atherosclerosis, thrombosis, liver cirrhosis, liver fibrosis, Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, or a disease, disorder or injury relating to dysmyelination or demyelination or the disease or disorder associated with abnormal activities of TRKA protein kinases.

In one aspect, the present invention provides, among other things, small molecule compounds and their salts or solvates in various crystalline forms and amorphous form as NGF receptor TrkA inhibitor and/or antagonist for the preparation of a medicament for the treatment and/or prevention of diseases associated, directly or indirectly with modulation of activity or expression of TrkA protein kinase or activity in certain patient populations with following cancer types with TrkA-positive mutations, fusions or fusion mutations or genetically abnormal TrkA kinase activity, that can be clinically diagnosed by current or future diagnostic tools, for examples, pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas.

In one aspect, the present invention provide a compound of the following structure in various crystalline forms and amorphous form:

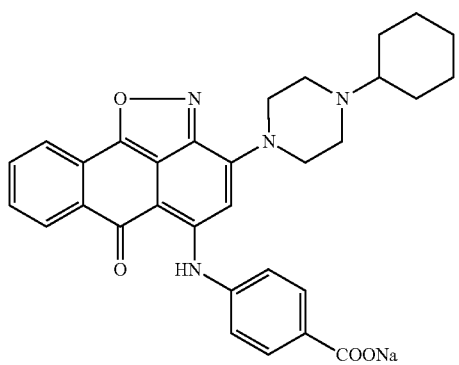 [SMILES: O=C(O)c1ccc(Nc2cc(N3CCN(C4CCCCC4)CC3)c3noc4c3c2C(=O)c2ccccc2-4)cc1]

Compound I

Sodium 4-((3-(4-cyclohexylpiperazin-1-yl)-6-oxo-6H-anthra[1,9-cd]isoxazol-5-yl)amino)benzoate In one embodiment, a crystalline polymorph of Compound I is crystalline polymorph Form A. In another embodiment, the crystalline polymorph exhibits an x-ray powder diffraction pattern having peak positions at degree two-theta of about: 10.0±0.3, 20.1±0.3, and 23.6±0.3. In another embodiment, the crystalline polymorph exhibits an x-ray powder diffraction pattern having peak positions at degree two-theta of one or more of about: 14.5±0.3 and 18.1±0.3, and about: 9.7±0.3 and 21.2±0.3. In a further embodiment, the crystalline polymorph exhibits an x-ray powder diffraction pattern having at least three, at least five, at least seven, at least ten, or all, of the following peak positions at degree two-theta of about: 7.160, 8.757, 9.820, 10.161, 12.459, 14.641, 15.219, 17.680, 18.240, 19.104, 20.220, 21.381, 22.579, 23.721, 24.898, 25.761, 25.522, 27.161, 28.321, 28.321, 29.481, 30.921, and 34.281.

In a further embodiment, a crystalline polymorph of Compound I of claim 1 is crystalline polymorph Form B. In a still further embodiment, the crystalline polymorph exhibits an x-ray powder diffraction pattern having three or more, or five or more, or seven or more, or all of, the peak positions at degree two-theta selected from the group consisting of about: 9.8±0.3, 10.2±0.3, 14.5±0.3, 17.8±0.3, 18.5±0.3, 19.6±0.3, 21.0±0.3, 21.7±0.3, and 23.1±0.3. In yet another embodiment, the crystalline polymorph exhibits an x-ray powder diffraction pattern having three or more, or five or more, or seven or more, or ten or more, or all of, the peak positions at degree two-theta selected from the group consisting of about: 9.8±0.3, 10.2±0.3, 14.5±0.3, 17.8±0.3, 18.5±0.3, 19.6±0.3, 21.0±0.3, 21.7±0.3, 23.1±0.3, 25.0±0.3, 25.6±0.3, 28.4±0.3, 29.4±0.3, 30.2±0.3, and 31.6±0.3.

In an additional embodiment, a crystalline polymorph of Compound I of claim 1 is crystalline polymorph Form C. In another embodiment, the crystalline polymorph exhibits an x-ray powder diffraction pattern having at least three, at least five, at least seven, or all, of the following peak positions at degree two-theta of about: 9.8±0.3, 10.2±0.3, 14.3±0.3, 17.4±0.3, 18.2±0.3, 18.9±0.3, 19.2±0.3, 22.1±0.3, 22.7±0.3, and 29.1±0.3. In still another embodiment, the crystalline polymorph exhibits an x-ray powder diffraction pattern having at least three, at least five, at least seven, at least ten, or all, of the following peak positions at degree two-theta of about: 9.0±0.3, 9.8±0.3, 10.2±0.3, 14.3±0.3, 15.9±0.3, 17.4±0.3, 18.2±0.3, 18.9±0.3, 19.2±0.3, 19.6±0.3, 20.2±0.3, 21.3±0.3, 22.1±0.3, 22.7±0.3, 24.7±0.3, 28.3±0.3, 28.9±0.3, 29.1±0.3, and 30.1±0.3.

In some embodiments, the crystalline polymorph of Compound I is polymorph Form D. In some other embodiments, the crystalline polymorph exhibits an x-ray powder diffraction pattern having peak positions at degree two-theta of about: 5.6±0.3, 26.0±0.3, and 26.7±0.3. In some additional embodiments, the crystalline polymorph exhibits an x-ray powder diffraction pattern having peak positions at degree two-theta of about: 8.5±0.3 and 19.3±0.3. In some further embodiments, the crystalline polymorph exhibits an x-ray powder diffraction pattern having at least three, at least five, at least seven, at least ten, or all, of the following peak positions at degree two-theta of about: 5.58, 7.43, 8.45, 9.21, 11.23, 11.98, 14.86, 17.025, 18.91, 22.80, 26.03, and 26.72.

In particular embodiments, the crystalline polymorph of Compound I is polymorph Form E. In other embodiments, the crystalline polymorph exhibits an x-ray powder diffraction pattern the peak positions at degree two-theta of about: 5.6±0.3, 14.4±0.3, and 23.5±0.3. In further embodiments, the crystalline polymorph exhibits an x-ray powder diffraction pattern the peak positions at degree two-theta of about: 18.9±0.3 and 21.0±0.3. In yet further embodiments, the crystalline polymorph exhibits an x-ray powder diffraction pattern having three or more, five or more, seven or more, ten or more, or all of, the peak positions at degree two-theta selected from the group consisting of about: 5.570, 6.846, 8.552, 9.505, 11.786, 14.374, 17.060, 17.431, 18.006, 18.893, 19.971, 21.015, 22.347, 22.840, 23.528, 25.496, 26.393, 28.264, 29.563, 30.710, 32.263, and 34.045.

In still further embodiments, Compound I is in an amorphous form.

Additional embodiments include a combination of any of the foregoing embodiments and one or more pharmaceutically acceptable excipients. Other embodiments include a dosage form, such as a solid or semi-solid dosage form, comprising any of the foregoing crystal forms, amorphous forms, or combinations. In yet other embodiments, a dosage form comprising any of the foregoing crystal forms, amorphous forms, or combinations comprises one or more of a tablet, hard capsule, soft capsule, powder, suppository, and gel, or one or more of an injectable form, a transdermal patch, a sprayable form, and an implantable depot.

Other embodiments are a use of any of the foregoing embodiments in making a dosage form for inhibiting, or for inhibiting, a NGF receptor, TrkA. Still other embodiments are a use of any of the foregoing embodiments in making a dosage form for treating a disorder, disease or condition selected from the group consisting of pain (i.e, reducing pain for a subject in need thereof, including acute pain, chronic pain, inflammatory pain, neuropathic pain, cancer pain, and generalized pain disorder), cancer (e.g., pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas), atopic dermatitis, psoriasis, skin diseases, itch, liver fibrosis, liver cirrhosis, scabies, pityriasis, inflammatory bowel disease, inflammatory arthritis, asthma, human airway diseases, Chagas' disease, parasitic diseases, Alzheimer's, restenosis, atherosclerosis, thrombosis, liver cirrhosis, liver fibrosis, Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, or a disease, disorder or injury relating to dysmyelination or demyelination or the disease or disorder associated with abnormal activities of TrkA protein kinases or fusions or mutations of TrkA (NTRK1) protein, with therapeutic effective amount of the compound as described above, or a salt, solvate, or physiologically functional derivative thereof.

Surprisingly, the Compound I's oral bioavailbility is dramatically increased to about 90 to 100% in rat, which represents a significant improvement compared to about less than 20% oral bioavailability in rat of the free acid Compound 701.

In another aspect, the invention provides pharmaceutical compositions comprising the compound described above, and a pharmaceutically acceptable vehicle.

In another aspect, the invention provides a method of use of Compound I in medical treatment and prevention.

In another aspect, the invention provides a method of use of Compound I in medical treatment and prevention of pain (i.e, reducing pain for a subject in need thereof, including acute pain, chronic pain, inflammatory pain, neuropathic pain, cancer pain, and generalized pain disorder), cancer (e.g., pancreatic cancer, prostate cancer or metastasis, breast cancer, hepatocellular carcinoma, intrahepatic cholangiocarcinoma, liver cancer, ovarian cancer, thyroid cancer, lung (small cell and non-small cell) cancer, colorectal cancer, glioblastoma, spitz tumors, spitzoid melanomas, acute myelogenous leukemia, endometrial cancer, skin cancer, oral cancer, bone cancer, melanoma, gastric cancer, esophageal cancer, gastrointestinal cancer, brain cancer or human neuroblastoma, medulloblastoma, retinoblastoma, leukemia, lymphoma, malignant mesothelioma, bladder cancer, squamous cell carcinomas), atopic dermatitis, psoriasis, skin diseases, itch, liver fibrosis, liver cirrhosis, scabies, pityriasis, inflammatory bowel disease, inflammatory arthritis, asthma, human airway diseases, Chagas' disease, parasitic diseases. Alzheimer's, restenosis, atherosclerosis, thrombosis, liver cirrhosis, liver fibrosis, Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, or a disease, disorder or injury relating to dysmyelination or demyelination or the disease or disorder associated with abnormal activities of TrkA protein kinases or fusions or mutations of TrkA (NTRK1) protein, with combination of (a) therapeutic effective amount of the compound as described above, or a salt, solvate, or ester, prodrug, or physiologically functional derivative thereof, and either (b1) an opioid analgesic or at least one analgesic agent that acts by a mechanism different from a Trk antagonist or, (b2) an existing or approved anti-cancer agent or chemotherapeutic or at least one existing or approved anti-cancer agent.

In another aspect, the invention provides a method for preparing Compound I described above.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound I, wherein the pharmaceutical composition is formulated in a unit dosage form selected from the group consisting of: an oral unit dosage form (including powder, tablets, pills, pellets, capsules, powders, lozenges, granules, solutions, suspensions, emulsion, syrups, elixirs, sustained-release formulations, aerosols, sprays and caplet), an inhalational unit dosage form (including spray, aerosol, inhaler, neulizer, smoking and vaporizer), a parenteral unit dosage form (including intradermal, intramuscular, intraosseous, intraperitoneal, intravenous, epidural, intracardiac, intraocular, intra-articular, subcutaneous and intrathecal injection unit dosage forms), a topical unit dosage form (including cream, gel, liiment or balm, lotion or ointment, ear drops, eye drops, skin patch and vaginal rings), an intranasal unit dosage form, a suppository unit dosage form (including vaginal, douche, pessary, and rectal), an epidural unit dosage form, a sublingual unit dosage form (including lozenge and troche), and an intracerebral unit dosage form.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound 1, wherein the pharmaceutical composition is formulated in an oral unit dosage form comprising from about 0.02 mg of the compound per kg of body weight to about 60 mg of the compound per kg of body weight.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound I, wherein the pharmaceutical composition is formulated in an intravenous unit dosage form comprising from about 0.002 mg of the compound per kg of body weight to about 60 mg of the compound per kg of body weight.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound I, wherein the pharmaceutical composition is formulated in an intranasal unit dosage form comprising from about 0.002 mg of the compound per kg of body weight to about 6 mg of the compound per kg of body weight.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound I, wherein the pharmaceutical composition is formulated in a suppository unit dosage form comprising from about 0.001 mg of the compound per kg of body weight to about 50 mg of the compound per kg of body weight and comprise active ingredient in the range of about 0.5% to about 10% by weight.

In another aspect, the invention provides a method for treating a disease, disorder, symptom, or condition associated with irregular TrkA activity, or fusion or mutation of TrkA protein or NTRK1 gene in a patient suffering therefrom, comprising administering to the patient a pharmaceutical composition, comprising a therapeutically effective amount of Compound I, wherein the pharmaceutical composition is formulated in a unit dosage form selected from the group consisting of: a parenteral unit dosage form (including intradermal, intramuscular, intraosseous, intraperitoneal, intravenous, epidural, intracardiac, intraocular, intra-articular, subcutaneous and intrathecal injection unit dosage forms), a topical unit dosage form (including cream, gel, liiment or balm, lotion or ointment, ear drops, eye drops, skin patch and vaginal rings), an intranasal unit dosage form, a suppository unit dosage form (including vaginal, douche, pessary, and rectal), an epidural unit dosage form, a sublingual unit dosage form (including lozenge and troche), and an intracerebral unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form, wherein said unit dosage forms comprise from about 0.001 mg of the compound per kg of body weight to about 60 mg of the compound per kg of body weight.

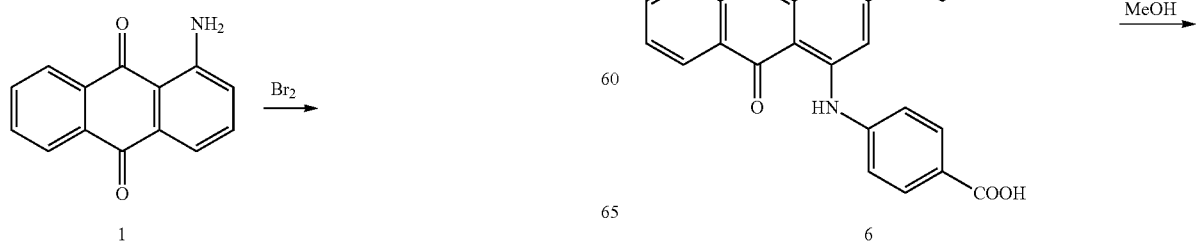

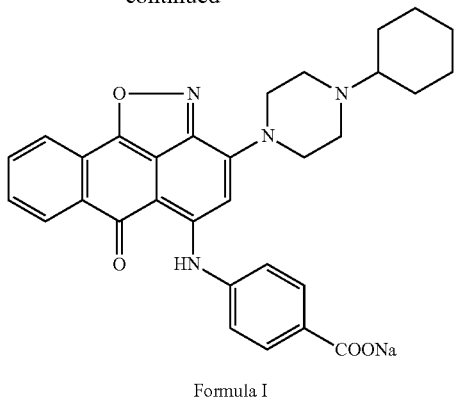

Formula I

In another aspect, the invention provides most stable polymorphic forms of Compound I and preparation processes.

DETAILED DESCRIPTION

Figure 1:
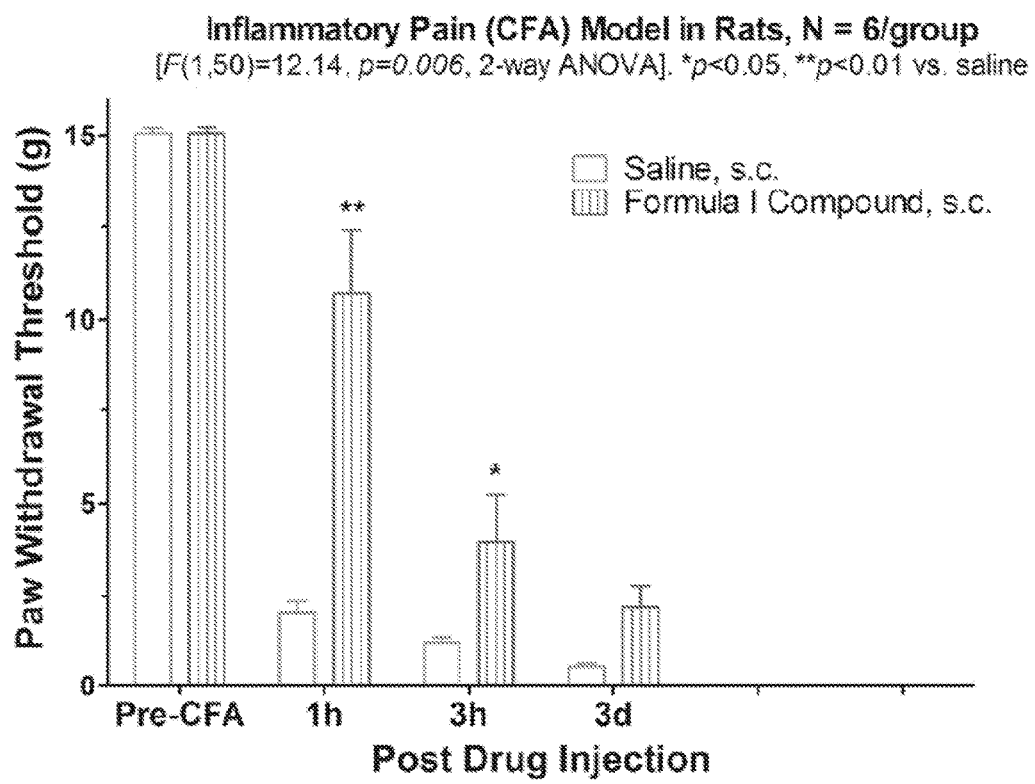
FIG. 1 is a graph showing time-dependent pain relieving effect of Compound I (s.c.) in CFA-induced rat inflammatory pain.

It should be understood that singular prepositions such as "a," "an," and "the," are often used for convenience, however, all instances of the singular are intended to encompass the plural unless otherwise indicated either explicitly or from context. Further, it should be understood that all references, including journal articles, books, patents, technical documents, and the like, mentioned in this disclosure are hereby incorporated by reference in their entirety and for all purposes.

Furthermore, all numerical data points should be understood to be modified by the term "about" as will be elaborated upon in the disclosure.

Definitions

The term "physiologically functional derivative(s)" as used herein refers to any physiologically tolerated derivative of a compound of the present invention, for example, an ester or prodrug, which, upon administration to a mammal, e.g., a human, are transformed directly or indirectly to Compound I, or an active metabolite thereof. Physiologically functional derivatives include prodrugs of the compounds of the present invention. Examples of prodrug are described in H. Okada et al., Chem. Pharm. Bull. 1994, 42, 57-61. Such prodrugs can be metabolized in vivo to a compound of the invention. These prodrugs may themselves be active or not.

Compounds of the present invention also include isotopically labeled compounds where one or more atoms have an atomic mass different from the atomic mass conventionally found in nature. Examples of isotopes that may be incorporated into the compounds include, but are not limited to, $^2H$, $^3H$, $^{13}C$, $^{14}C$, $^{15}N$, $^{17}O$, $^{18}O$, etc. Compounds may exist in unsolvated forms as well as solvated forms, including hydrated forms and as N-oxides. In general, the salt, hydrated, solvated, and N-oxide forms are within the scope of the present invention. Certain compounds of the present invention may exist in multiple crystalline forms or an amorphous form. In general, all physical forms are equivalent for the uses contemplated by the present invention and are intended to be within the scope of the present invention.

"Patient" or "subject" includes, but is not limited to, animals such as, for example, mammals. Preferably, the patient is a human.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Solvate" means a compound formed by solvation (the combination of solvent molecules with molecules or ions of the solute, i.e., a compound of the present invention), or an aggregate that consists of a solute ion or molecule (the compound of the present invention) with one or more solvent molecules.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Treating", "treat" or "treatment" of any disease or disorder refers, in some embodiments, to ameliorating or preventing the disease or disorder (i.e., arresting, preventing, holding or reducing the development of the disease or at least one of the clinical symptoms thereof). In other embodiments "treating", "treat" or "treatment" refers to ameliorating at least one physical parameter, which may not be discernible by the patient. In yet other embodiments, "treating", "treat" or "treatment" refers to inhibiting, or holding or preventing the progress of, the disease or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

The phrases "an effective amount" and "an amount sufficient to" refer to amounts of a biologically active agent that produce an intended biological activity.

The term "co-administer" or "co-administering" when used in reference to the administration of Trk (i.e., TrkA) antagonists and other agents indicates that the antagonist and other agent(s) are administered in a coordinated fashion so that there is at least some chronological overlap in their physiological activity on the subject. Thus, a TrkA antagonist can be administered simultaneously and/or sequentially with another agent. In sequential administration, there may even be some substantial delay (e.g., minutes or even hours or days) before administration of the second agent as long as the first administered agent is exerting some physiological effect on the organism when the second administered agent is administered or becomes active in the subject.

The term "reducing pain," as used herein, refers to decreasing the level of pain a subject perceives relative to the level of pain the subject would have perceived were it not for the intervention. Where the subject is a person, the level of pain the person perceives can be assessed by asking him or her to describe the pain or compare it to other painful experiences. Alternatively, pain levels can be determined by measuring the subject's physical responses to the pain, such as the release of stress-related factors or the activity of pain-transducing nerves in the peripheral nervous system or the CNS. One can also determine pain levels by measuring the amount of a well-characterized analgesic required for a person to report that no pain is present or for a subject to stop exhibiting symptoms of pain. A reduction in pain can also be measured as an increase in the threshold at which a subject experiences a given stimulus as painful. In certain embodiments, a reduction in pain is achieved by decreasing "hyperalgesia," the heightened sensitivity to a noxious stimulus, and such inhibition can occur without impairing "nociception," the subject's normal sensitivity to a "noxious" stimulus.

As used with reference to pain reduction. "a subject in need thereof" refers to an animal or person, preferably a person, expected to experience pain in the near future. Such animal or person may have an ongoing condition that is causing pain currently and is likely to continue to cause pain. Alternatively, the animal or person has been, is, or will be enduring a procedure or event that usually has painful consequences. Chronic painful conditions such as diabetic neuropathic hyperalgesia and collagen vascular diseases are examples of the first type; dental work, particularly that accompanied by inflammation or nerve damage, and toxin exposure (including exposure to chemotherapeutic agents) are examples of the latter type.

"Inflammatory pain" refers to pain arising from inflammation. Inflammatory pain often manifests as increased sensitivity to mechanical stimuli (mechanical hyperalgesia or tenderness). For examples, inflammatory pain is due to a condition selected from the group consisting of: burn, sunburn, arthritis, osteoarthritis, colitis, carditis, dermatitis, myositis, neuritis, mucositis, urethritis, cystitis, gastritis, pneumonitis, and collagen vascular disease.

"Neuropathic pain" refers to pain arising from conditions or events that result in nerve damage. "Neuropathy" refers to a disease process resulting in damage to nerves. "Causalgia" denotes a state of chronic pain following nerve injury. "Allodynia" refers to a condition in which a person experiences pain in response to a normally nonpainful stimulus, such as a gentle touch. For examples, neuropathic pain is due to a condition selected from the group consisting of: causalgia, diabetes, diabetic peripheral neuropathy, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, anti-viral therapy, AIDS, and AIDS therapy. Neuropathic pain is due to an agent selected from the group consisting of: trauma, surgery, amputation, toxin, and chemotherapy.

As used herein, the term "generalized pain disorder" refers to a group of idiopathic pain syndromes (e.g., fibromyalgia, irritable bowel syndrome, and temporomandibular disorders), for which the pathogenic mechanism is currently unknown, characterized by diffuse or generalized pain, and for which a diagnosis of inflammation or neuropathy as the direct cause of pain is excluded.

An "analgesic agent" refers to a molecule or combination of molecules that causes a reduction in pain.

The difference between "acute" and "chronic" pain is one of timing: acute pain is experienced soon (e.g., generally within about 48 hours, more typically within about 24 hours, and most typically within about 12 hours) after the occurrence of the event (such as inflammation or nerve injury) that led to such pain. By contrast, there is a significant time lag between the experience of chronic pain and the occurrence of the event that led to such pain. Such time lag is generally at least about 48 hours after such event, more typically at least about 96 hours after such event, and most typically at least about one week after such event. Examples of chronic pain are musculoskeletal pain (back pain, low back pain, osteoarthritis pain), chronic headache, migraine, neck pain, hip pain, shoulder pain, neuropathic pain, interstitial cystitis pain, chronic inflammatory pain, prostatitis pain, cancer pain, endometriosis pain, post-herpetic neuralgia, diabetic peripheral neuropathy, visceral pain, abdominal pain, central pain, generalized pain disorders and combination of thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The term "cancer" refers to or describes the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, hepatocellular carcinoma, malignant hepatoma, colorectal cancer, endometrial cancer, kidney cancer, prostate cancer, thyroid cancer, neuroblastoma, pancreatic cancer, glioblastoma multiforme, cervical cancer, stomach cancer, bladder cancer, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a compound" includes a combination of two or more compounds or molecules, and the like.

In one aspect of the present invention, a compound has the following structure:

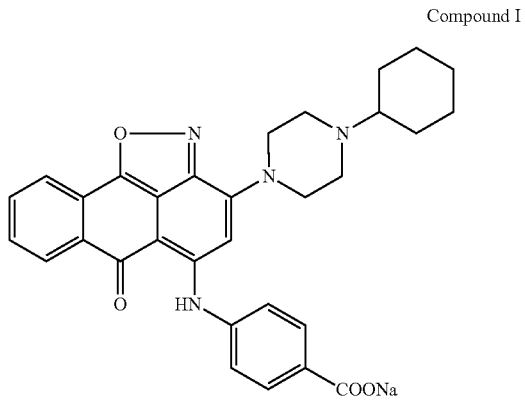

Compound I

Sodium 4-((3-(4-cyclohexylpiperazin-1-yl)-6-oxo-6H-anthra[1,9-cd]isoxazol-5-yl)amino)benzoate The present invention includes amorphous form of Compound I as well as various polymorphic forms of Compound I. Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

In one embodiment, the crystalline forms are characterized by the interlattice plane intervals determined by a X-ray powder diffraction pattern. The spectrum of XRD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. In one embodiment, the intensity of about 81% to 100% is very strong; the intensity of about 61% to 80% is strong; the intensity of about 41% to 60% is medium; the intensity of about 21% to 40% is weak; and the intensity of about 1% to 20% is very weak. The characteristic peaks of a given XRD can be selected according to the peak locations and their relative intensity to conveniently distinguish this crystalline structure from others.

Those skilled in the art recognize that the measurements of the XRD peak locations and/or intensity for a given crystalline form of the same compound will vary within a margin of error. The values of degree 2θ allow appropriate error margins. Typically, the error margins are represented by "±". For example, the degree 2θ of about "9.7±0.3" denotes a range from about 9.7±0.3, i.e., about 10.0, to about 9.7-0.3, i.e., about 9.4. Depending on the sample preparation techniques, the calibration techniques applied to the instruments, human operational variation, and etc, those skilled in the art recognize that the appropriate error of margins for a XRD can be ±0.5; ±0.4; ±0.3; ±0.2; ±0.1; ±0.05; or less.

The term "substantially similar" as used herein means an analytical spectrum, such as XRD pattern, $^1$H-NMR spectrum, FT-IR spectrum, Raman spectrum, TGA thermogram, etc., which resembles the reference spectrum to a great degree in both the peak locations and their intensity.

In one specific embodiment, a process for the preparation of Compound I, comprising the following steps:

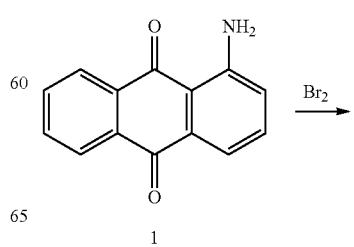

1

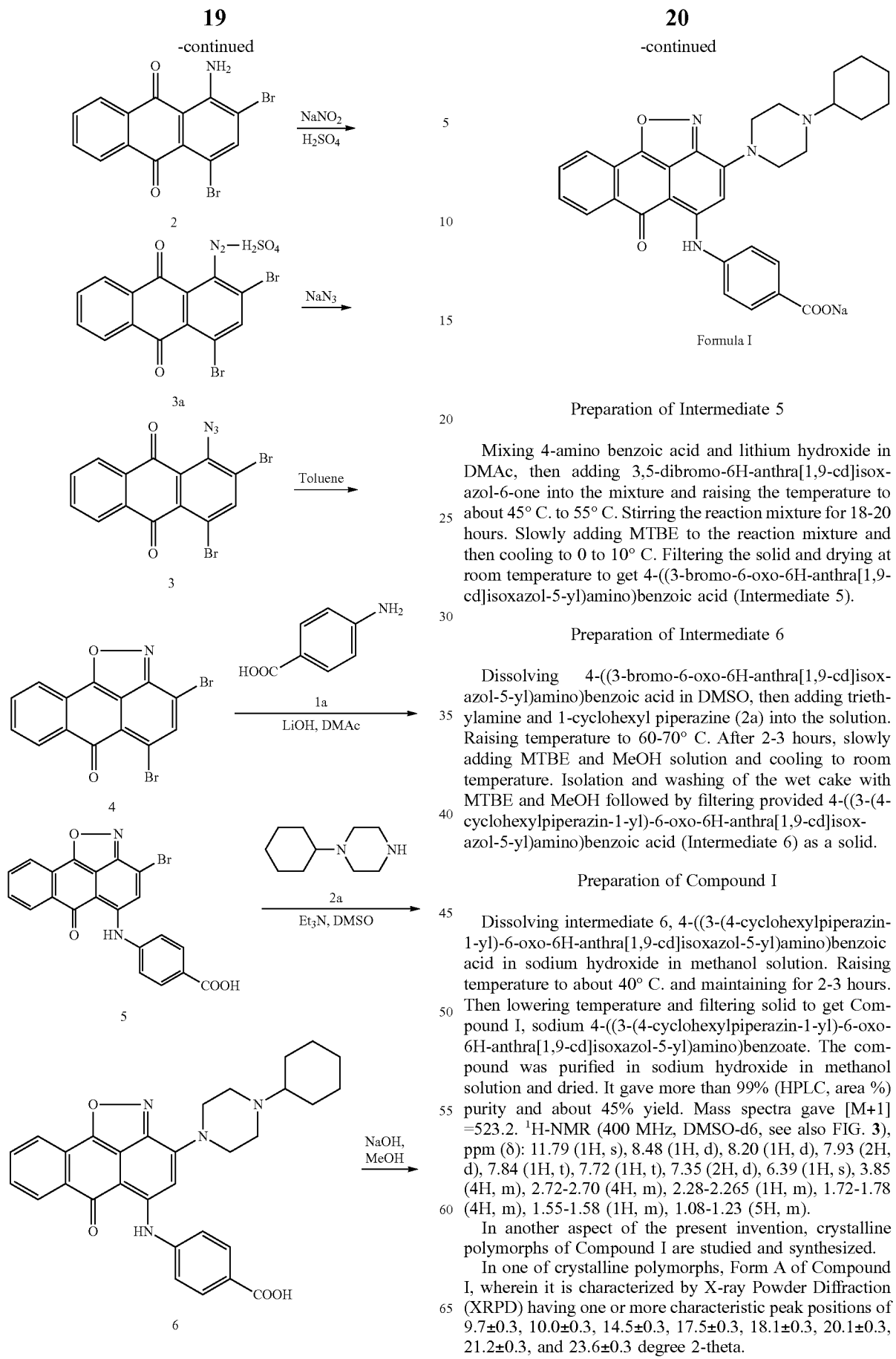

Preparation of Intermediate 5

Mixing 4-amino benzoic acid and lithium hydroxide in DMAc, then adding 3,5-dibromo-6H-anthra[1,9-cd]isoxazol-6-one into the mixture and raising the temperature to about 45° C. to 55° C. Stirring the reaction mixture for 18-20 hours. Slowly adding MTBE to the reaction mixture and then cooling to 0 to 10° C. Filtering the solid and drying at room temperature to get 4-((3-bromo-6-oxo-6H-anthra[1,9-cd]isoxazol-5-yl)amino)benzoic acid (Intermediate 5).

Preparation of Intermediate 6

Dissolving 4-((3-bromo-6-oxo-6H-anthra[1,9-cd]isoxazol-5-yl)amino)benzoic acid in DMSO, then adding triethylamine and 1-cyclohexyl piperazine (2a) into the solution. Raising temperature to 60-70° C. After 2-3 hours, slowly adding MTBE and MeOH solution and cooling to room temperature. Isolation and washing of the wet cake with MTBE and MeOH followed by filtering provided 4-((3-(4-cyclohexylpiperazin-1-yl)-6-oxo-6H-anthra[1,9-cd]isoxazol-5-yl)amino)benzoic acid (Intermediate 6) as a solid.

Preparation of Compound I

Figure 3:
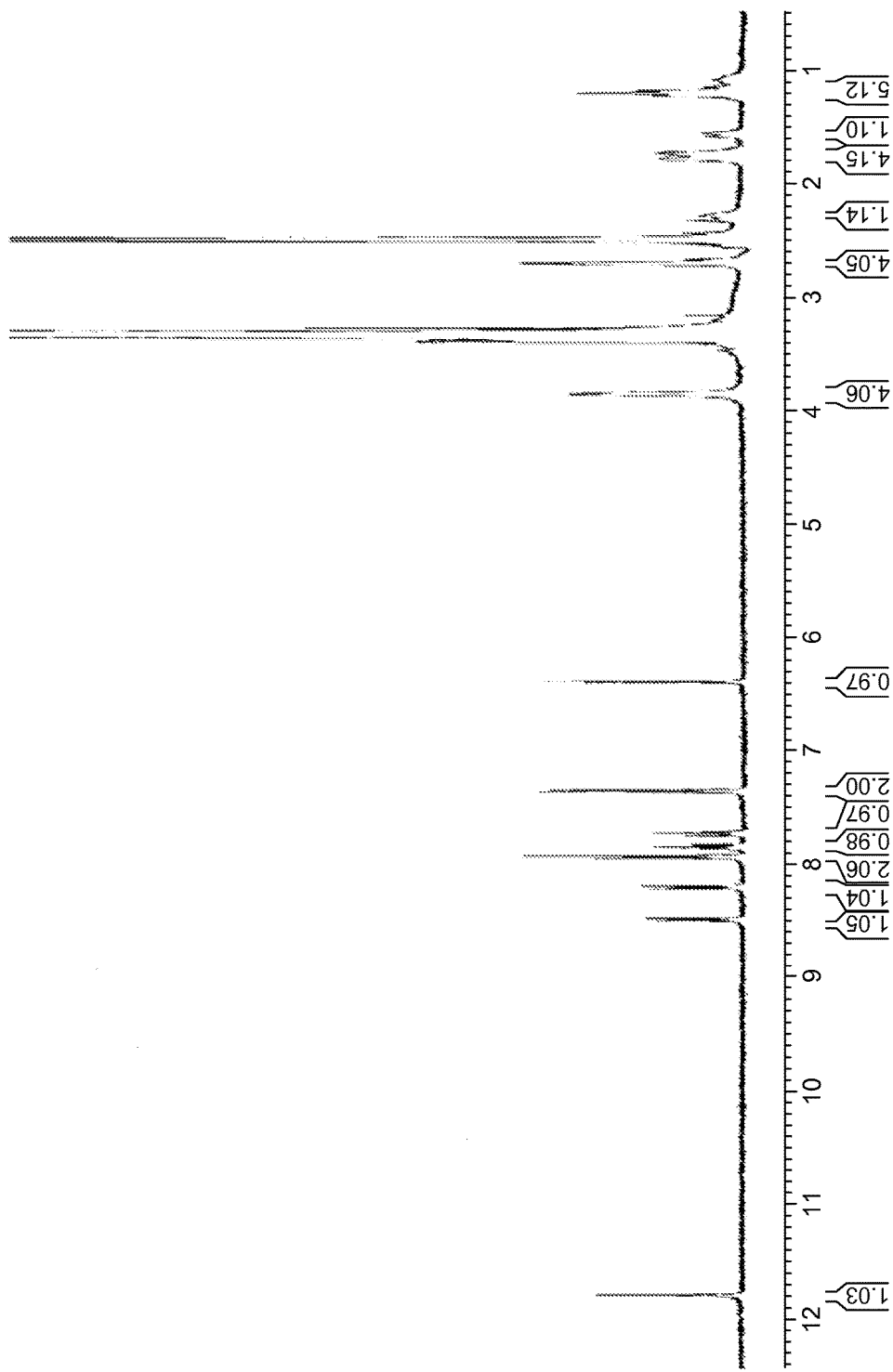
FIG. 3 is 1H-NMR spectra of the polymorph Form A of Compound I.

Dissolving intermediate 6, 4-((3-(4-cyclohexylpiperazin-1-yl)-6-oxo-6H-anthra[1,9-cd]isoxazol-5-yl)amino)benzoic acid in sodium hydroxide in methanol solution. Raising temperature to about 40° C. and maintaining for 2-3 hours. Then lowering temperature and filtering solid to get Compound I, sodium 4-((3-(4-cyclohexylpiperazin-1-yl)-6-oxo-6H-anthra[1,9-cd]isoxazol-5-yl)amino)benzoate. The compound was purified in sodium hydroxide in methanol solution and dried. It gave more than 99% (HPLC, area %) purity and about 45% yield. Mass spectra gave [M+1]=523.2. $^1$H-NMR (400 MHz, DMSO-d6, see also FIG. 3), ppm (δ): 11.79 (1H, s), 8.48 (1H, d), 8.20 (1H, d), 7.93 (2H, d), 7.84 (1H, t), 7.72 (1H, t), 7.35 (2H, d), 6.39 (1H, s), 3.85 (4H, m), 2.72-2.70 (4H, m), 2.28-2.265 (1H, m), 1.72-1.78 (4H, m), 1.55-1.58 (1H, m), 1.08-1.23 (5H, m).

In another aspect of the present invention, crystalline polymorphs of Compound I are studied and synthesized.

In one of crystalline polymorphs, Form A of Compound I, wherein it is characterized by X-ray Powder Diffraction (XRPD) having one or more characteristic peak positions of 9.7±0.3, 10.0±0.3, 14.5±0.3, 17.5±0.3, 18.1±0.3, 20.1±0.3, 21.2±0.3, and 23.6±0.3 degree 2-theta.

The crystalline polymorph Form A of Compound I is further characterized by XRPD having one or more peak positions of 7.0±0.3, 8.6±0.3, 9.7±0.3, 10.0±0.3, 12.3±0.3, 14.5±0.3, 15.1±0.3, 17.5±0.3, 18.1±0.3, 19.0±0.3, 20.1±0.3, 21.2±0.3, 22.4±0.3, 23.6±0.3, 24.6±0.3, 25.6±0.3, 26.5±0.3, 28.2±0.3, 29.4±0.3, 30.6±0.3, 34.1±0.3 and 35.0±0.3 degree 2-theta.

In another aspect, the present invention comprises another crystalline form (Form B) of the Compound I described above, XRPD peaks at one or more of 9.8±0.3, 10.2±0.3, 14.5±0.3, 17.8±0.3, 18.5±0.3, 19.6±0.3, 21.0±0.3, 21.7±0.3, 23.1±0.3, degree 2-theta.

Figure 11:
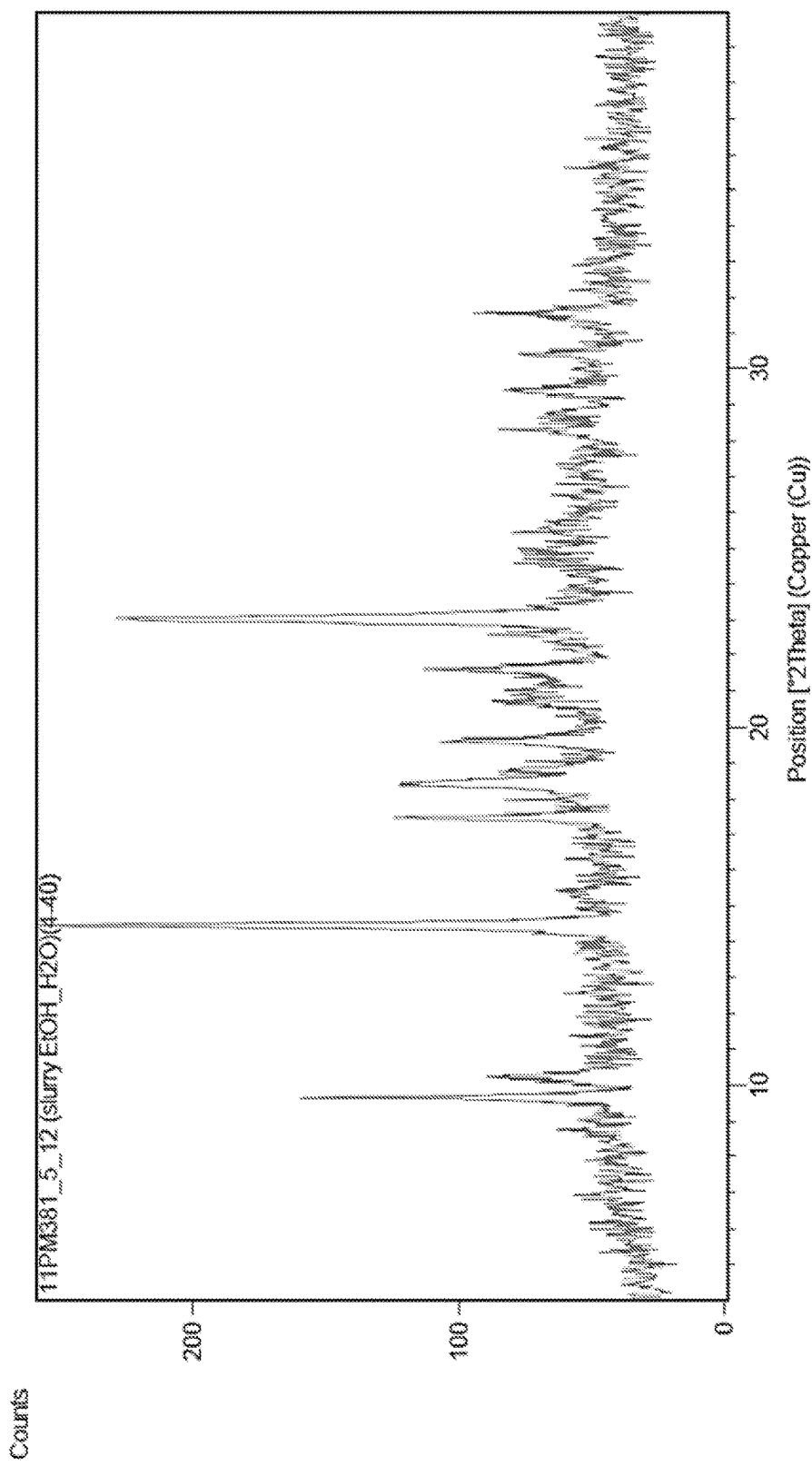
FIG. 11 is X-ray powder diffraction (XRPD) spectra of the polymorphic form, Form B of Compound I.
Figure 12:
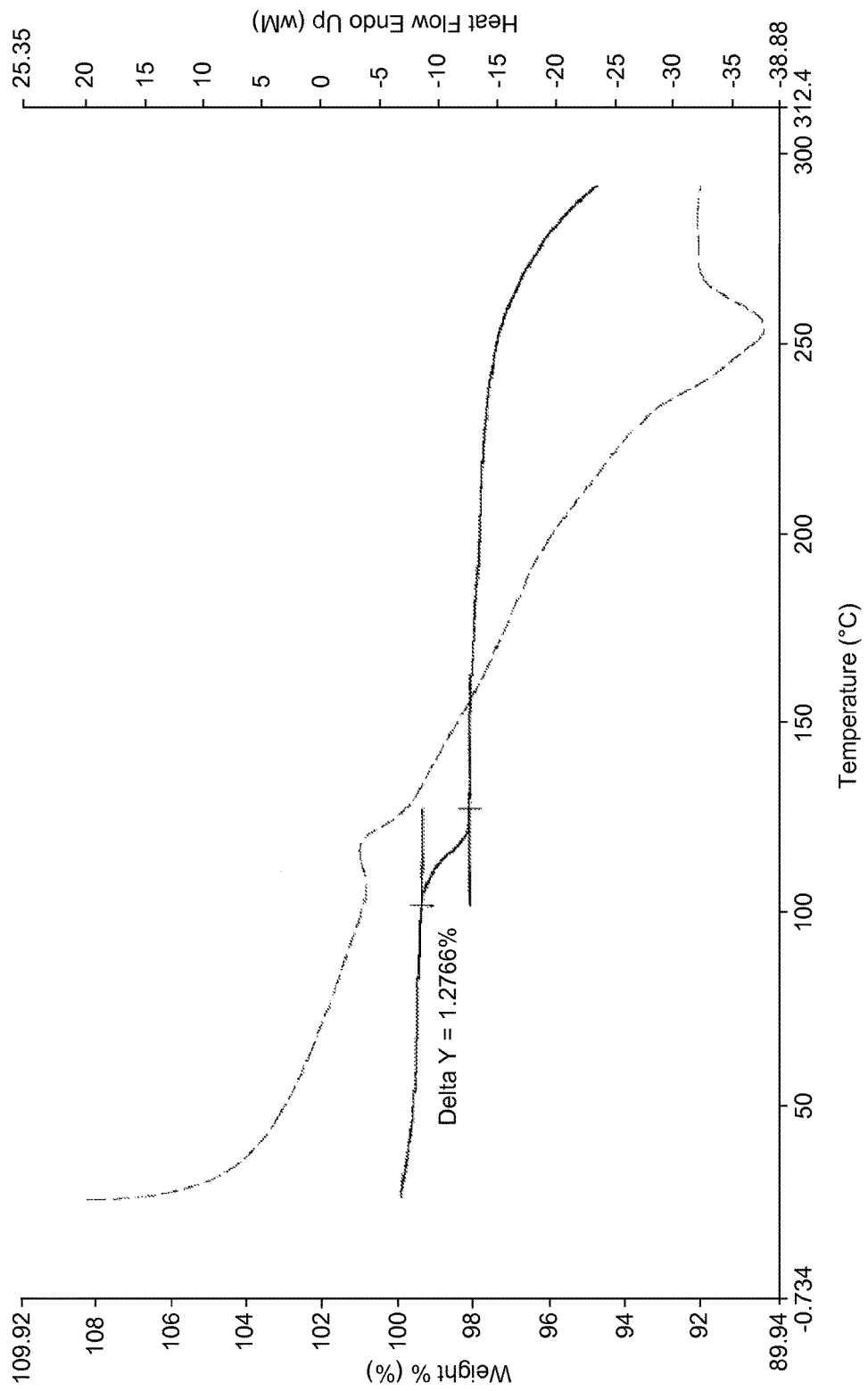
FIG. 12 is STA spectra of the polymorphic form, Form B of Compound I.

In another aspect, the present invention comprises another crystalline form (Form B) of the Compound I described above, XRPD peaks at one or more of 9.8±0.3, 10.2±0.3, 14.5±0.3, 17.8±0.3, 18.5±0.3, 19.6±0.3, 21.0±0.3, 21.7±0.3, 23.1±0.3, 25.0±0.3, 25.6±0.3, 28.4±0.3, 29.4±0.3, 30.2±0.3, 31.6±0.3 degree 2-theta. An example of Form B is given in FIG. 11. Form B can be a hydrate or hemi-hydrate polymorphic form, however, experimental results are consistant with the proposition that Form B does not conver to Form A upon simple heating or drying.

In another aspect, the present invention comprises a third crystalline form (Form C) of the Compound I described above, XRPD peaks at one or more of 9.8±0.3, 10.2±0.3, 14.3±0.3, 17.4±0.3, 18.2±0.3, 18.9±0.3, 19.2±0.3, 22.1±0.3, 22.7±0.3, 29.1±0.3, degree 2-theta.

Figure 14:
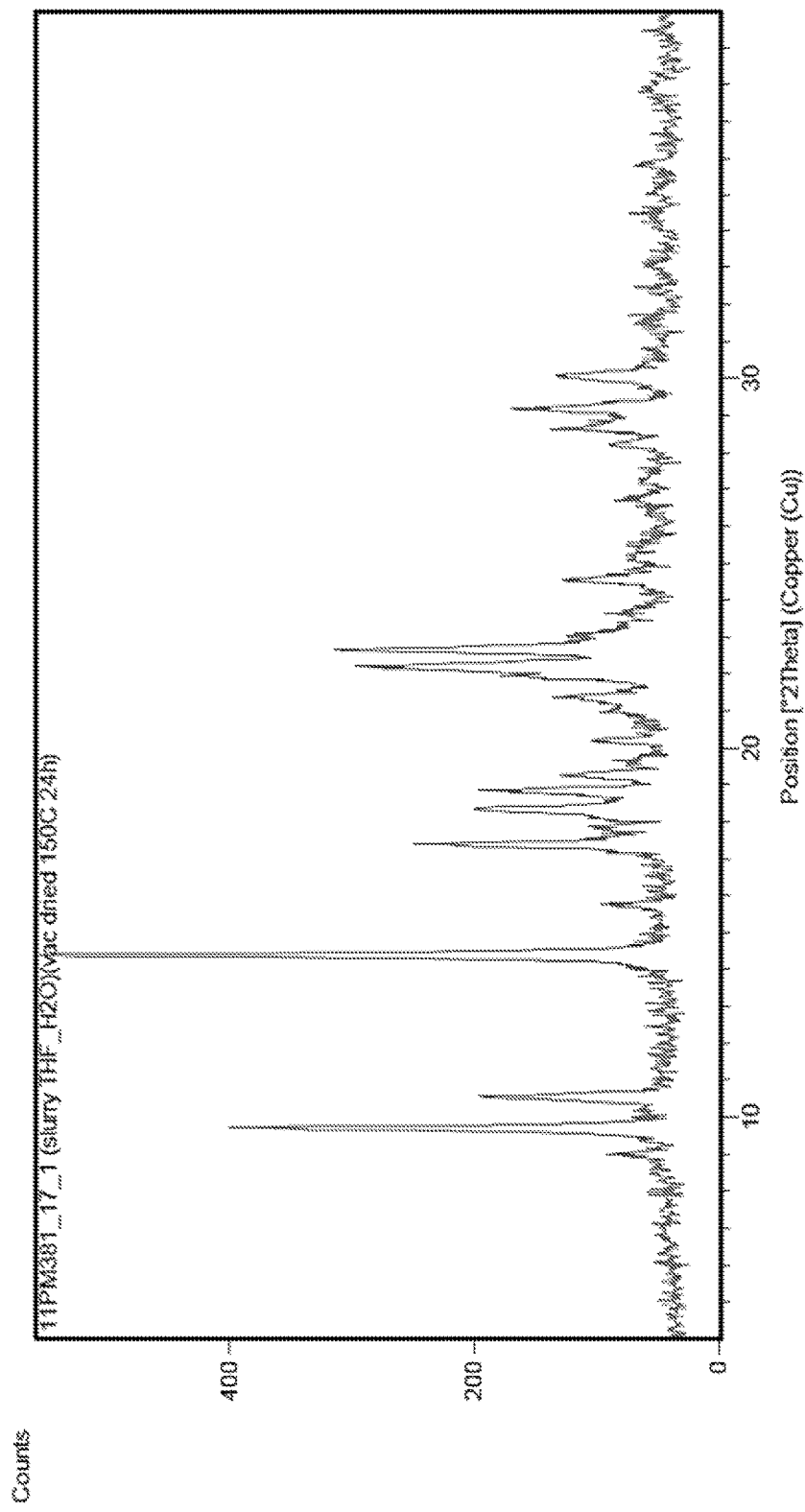
FIG. 14 is X-ray powder diffraction (XRPD) spectra of the polymorphic form, Form C of Compound I.

In another aspect, the present invention comprises a third crystalline form (Form C) of the Compound I described above, XRPD peaks at one or more of 9.0-0.3, 9.8±0.3, 10.2±0.3, 14.3±0.3, 15.9±0.3, 17.4±0.3, 18.2±0.3, 18.9±0.3, 19.2±0.3, 19.6±0.3, 20.2±0.3, 21.3±0.3, 22.1±0.3, 22.7±0.3, 24.7±0.3, 28.3±0.3, 28.9±0.3, 29.1±0.3, 30.1±0.3 degree 2-theta. An example of Form C is given in FIG. 14.

In another aspect, the present invention comprises a third crystalline form (Form D) of the Compound I described above, XRPD peaks at one or more of 5.6±0.3, 8.5±0.3, 14.9±0.3, 17.0±0.3, 26.0±0.3, 26.7±0.3, degree 2-theta.

In another aspect, the present invention comprises a third crystalline form (Form D) of the Compound I described above, XRPD peaks at one or more of 5.6±0.3, 7.4±0.3, 8.5±0.3, 9.2±0.3, 11.2±0.3, 12.0±0.3, 14.9±0.3, 17.0±0.3, 18.9±0.3, 22.8±0.3, 26.0±0.3, 26.7±0.3, degree 2-theta. An example of Form D is given in FIG. 16.

Figure 15:
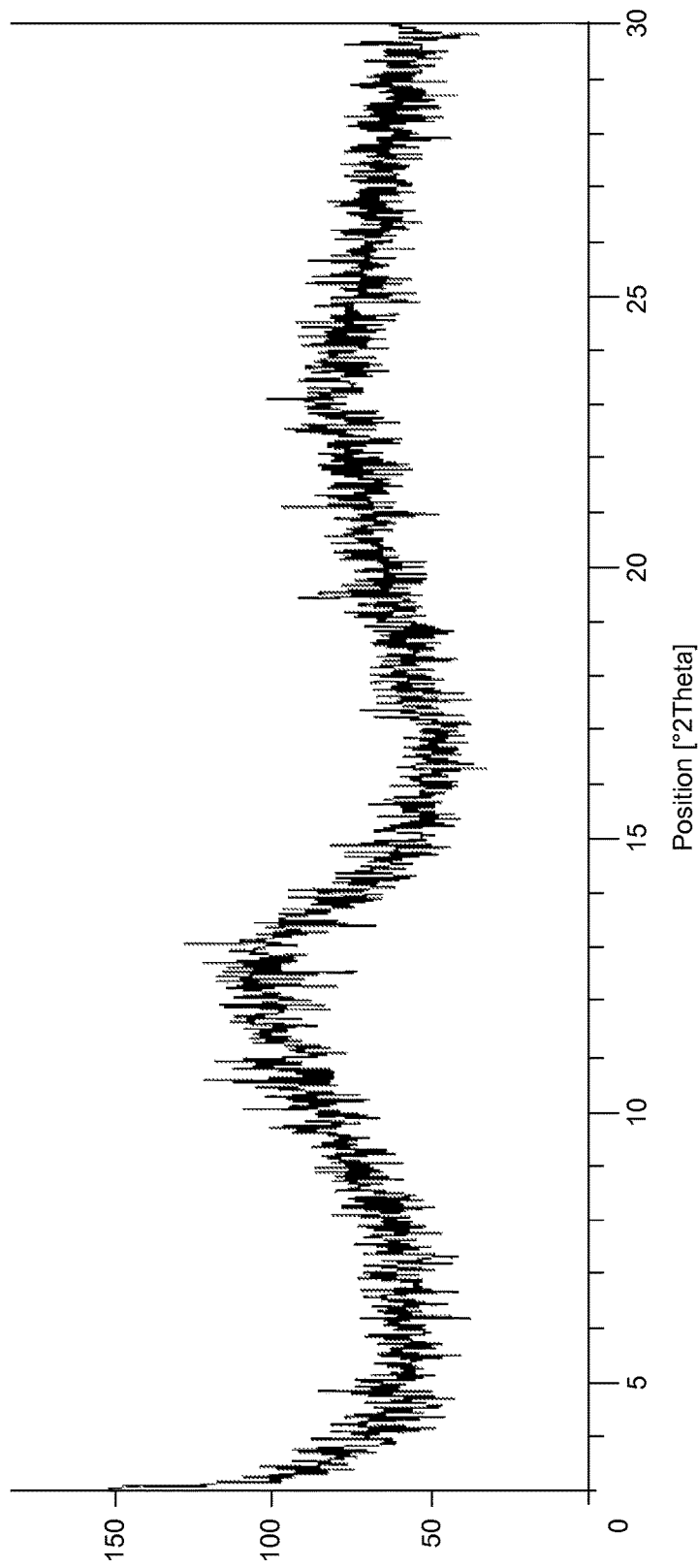
FIG. 15 is X-ray powder diffraction (XRPD) spectra of the amorphous Compound I.

An amorphous form of Compound I was also found and characterized by XRPD. An example of amprpjous of Compound I is given in FIG. 15.

In another aspect, the present invention comprises a method of producing the crystalline form of Compound I described above.

Example 1

Preparation of 4-((3-bromo-6-oxo-6H-anthra[1,9-cd] isoxazol-5-yl)amino)benzoic Acid About 70 g of 4-amino benzoic acid and 22 g of lithium hydroxide were mixed in 800 mL of DMAc. Then 100 g of 3,5-dibromo-6H-anthra[1,9-cd]isoxazol-6-one was dissolved in the pre-mixed solution. Nitrogen protection was applied to the reaction mixture at 45-55° C. for about 18-20 hours. After reaction completion was confirmed by HPLC, 30 mL of MTBE was slowly added to the reactor. Reaction mixture was then slowly cooled to 0-10° C. under nitrogen protection. Centrifuged the solid and washed with 18 mL of MTBE. Dried the wet cake under 25-30° C. to obtain about 69 g of 4-((3-bromo-6-oxo-6H-anthra[1,9-cd]isoxazol-5-yl)amino)benzoic acid.

Example 2

Preparation of 4-((3-(4-cyclohexylpiperazin-1-yl)-6-oxo-6H-anthra[1,9-cd]isoxazol-5-yl)amino)benzoic Acid About 70 g of 4-((3-bromo-6-oxo-6H-anthra[1,9-cd]isoxazol-5-yl)amino)benzoic acid was dissolved in 950 mL of DMSO. About 50 mL of TEA and 50 g of 1-cyclohexyl piperazine were added to the reaction. Temperature was raised to 60-70° C. After 2-3 hours, slowly added 500 mL of MTBE and MeOH (10:1) solution and adjusted the temperature to 40-50° C. The solid was centrifuged and washed by 100 mL of MTBE and MeOH solution and followed by 100 mL of MeOH. Solid was dried under reduced pressure at 25-30° C. for 12-24 hours to obtain the 4-((3-(4-cyclohexylpiperazin-1-yl)-6-oxo-6H-anthra[1,9-cd]isoxazol-5-yl)amino)benzoic acid at about 98% purity and about 91% yield.

Example 3

Figure 4:
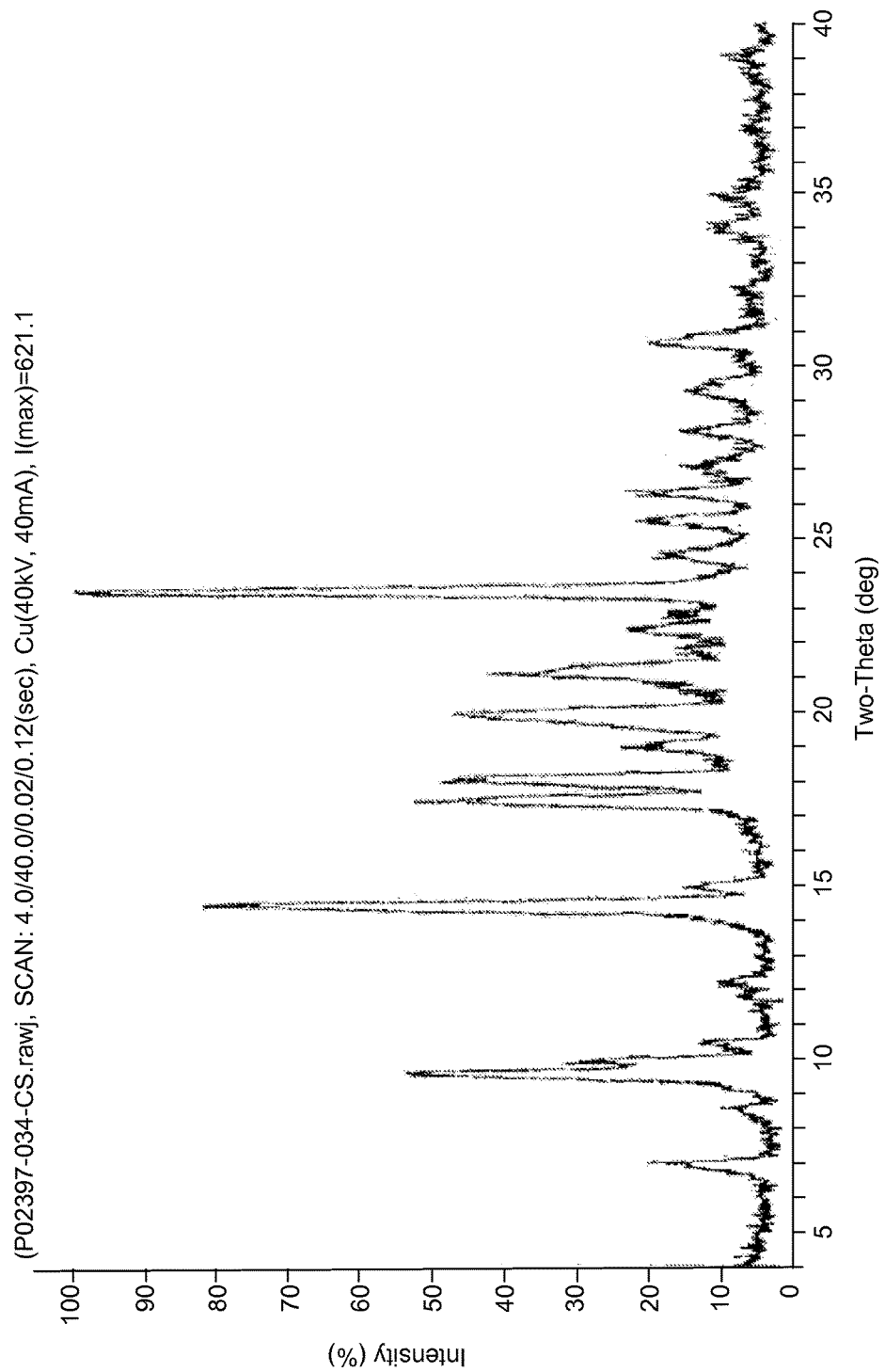
FIG. 4 is X-ray powder diffraction (XRPD) spectra of the polymorph Form A of Compound I.
Figure 5:
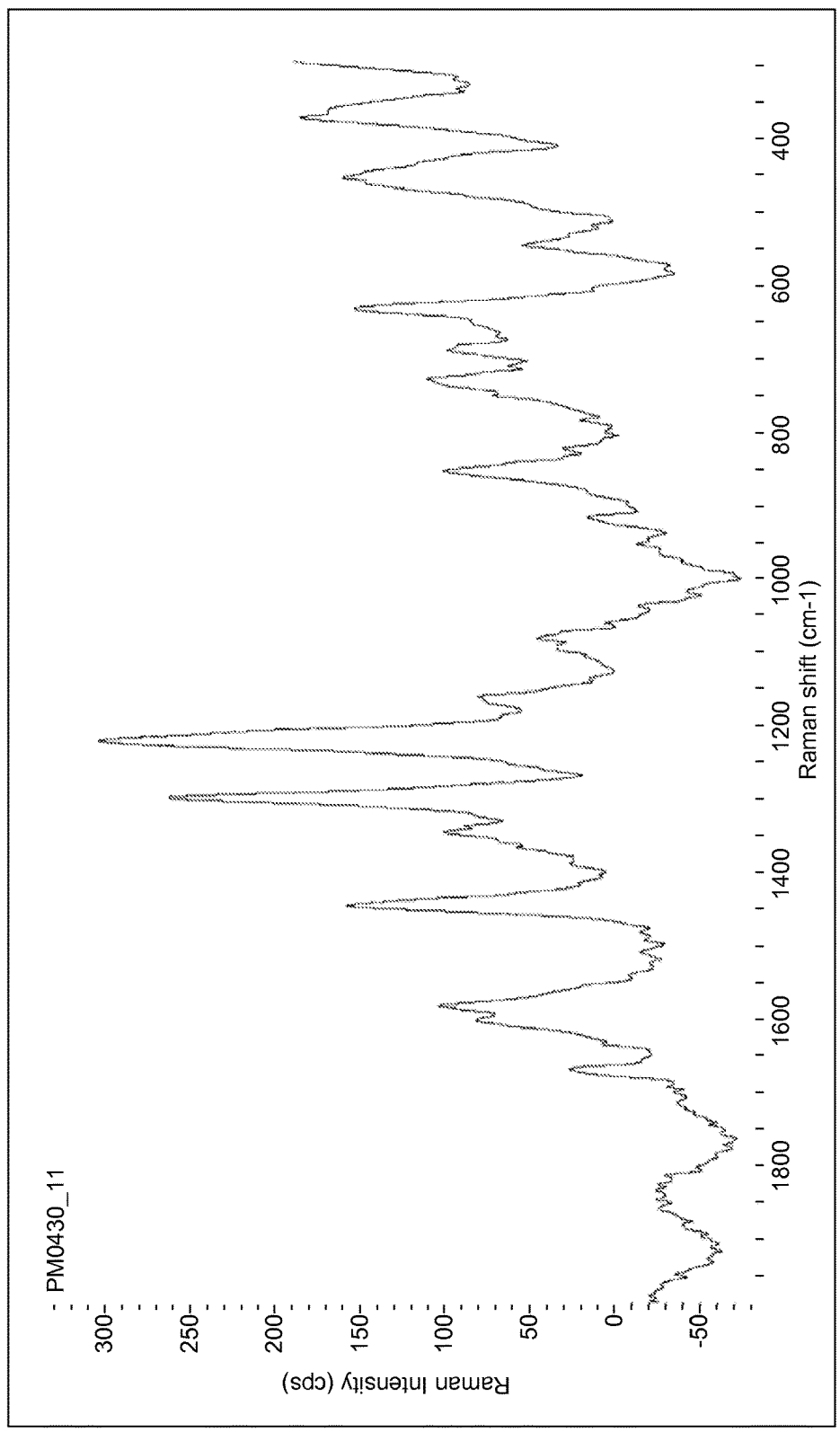
FIG. 5 is Raman spectra of the polymorph Form A of Compound I.

Preparation of sodium 4-((3-(4-cyclohexylpiperazin-1-yl-6-oxo-6H-anthra[1,9-cd]isoxazol-5-yl)amino) benzoate About 80 g of 4-((3-(4-cyclohexylpiperazin-1-yl)-6-oxo-6H-anthra[1,9-cd]isoxazol-5-yl)amino)benzoic acid was slurred in 2500 mL of 0.4 M NaOH/MeOH between 40-45° C. for 2-4 hours. After confirmed the reaction completion by HPLC, slowly cooled the reaction to room temperature. The solid was centrifuged and washed with 20 mL of MTBE. The wet cake was re-suspended in about 1000 mL of 0.1M NaOH in MeOH solution under room temperature. It was centrifuged and washed with 224 mL of MTBE again. The filtered solid was suspended in 996 mL of MTBE under room temperature for 1-2 hours. The solid was separated and dried at 25-30° C. under pressure for 12-24 hours to obtain the final desired product with purity more than 99% and about 90% yield. Mass spectra give [M+1]=523.2. $^1$H-NMR (400 MHz, DMSO-d6, see FIG. 3), ppm (δ): 11.79 (1H, s), 8.48 (1H, d), 8.20 (1H, d), 7.93 (2H, d), 7.84 (1H, t), 7.72 (1H t), 7.35 (2H, d), 6.39 (1H, s), 3.85 (4H, m), 2.72-2.70 (4H, m), 2.28-2.265 (1H, m), 1.72-1.78 (4H, m), 1.55-1.58 (1H, m), 1.08-1.23 (5H, m). Sodium content is 3.8%. The Raman spectrum is shown in FIG. 5. The XRPD, see Table below and FIG. 4, confirmed the polymorphic form.

TABLE 1

XRPD Table of the polymorphic form, Form A of Compound I.

| # | Angle 2-Theta° | d-value (Angstrom) | Intensity (%) |
|---|---|---|---|
| 1 | 7.160 | 12.3354 | 14.3 |
| 2 | 8.757 | 10.0899 | 22.4 |
| 3 | 9.820 | 9.0001 | 70.1 |
| 4 | 10.161 | 8.6986 | 88.1 |
| 5 | 10.522 | 8.4006 | 7.3 |
| 6 | 12.459 | 7.0985 | 14.5 |
| 7 | 14.641 | 6.0454 | 82.0 |
| 8 | 15.219 | 5.8170 | 22.8 |
| 9 | 17.680 | 5.0124 | 41.0 |
| 10 | 18.240 | 4.8598 | 73.0 |

TABLE 1-continued

XRPD Table of the polymorphic form, Form A of Compound I.

| # | Angle 2-Theta° | d-value (Angstrom) | Intensity (%) |
|---|---|---|---|
| 11 | 19.104 | 4.6420 | 14.2 |
| 12 | 20.220 | 4.3883 | 100.0 |
| 13 | 21.381 | 4.1525 | 33.3 |
| 14 | 22.579 | 3.9347 | 10.1 |
| 15 | 23.721 | 3.7478 | 99.7 |
| 16 | 24.898 | 3.6733 | 11.8 |
| 17 | 25.761 | 3.4555 | 17.8 |
| 18 | 25.522 | 3.3581 | 13.6 |
| 19 | 27.161 | 3.2804 | 17.7 |
| 20 | 28.321 | 3.1487 | 10.5 |
| 21 | 29.481 | 3.0273 | 12.8 |
| 22 | 29.781 | 2.9976 | 8.7 |
| 23 | 30.478 | 2.9306 | 7.7 |
| 24 | 30.921 | 2.8896 | 18.6 |
| 25 | 34.281 | 2.6137 | 12.1 |
| 26 | 35.120 | 2.5532 | 8.0 |
| 27 | 35.483 | 2.5279 | 6.0 |

Figure 7:
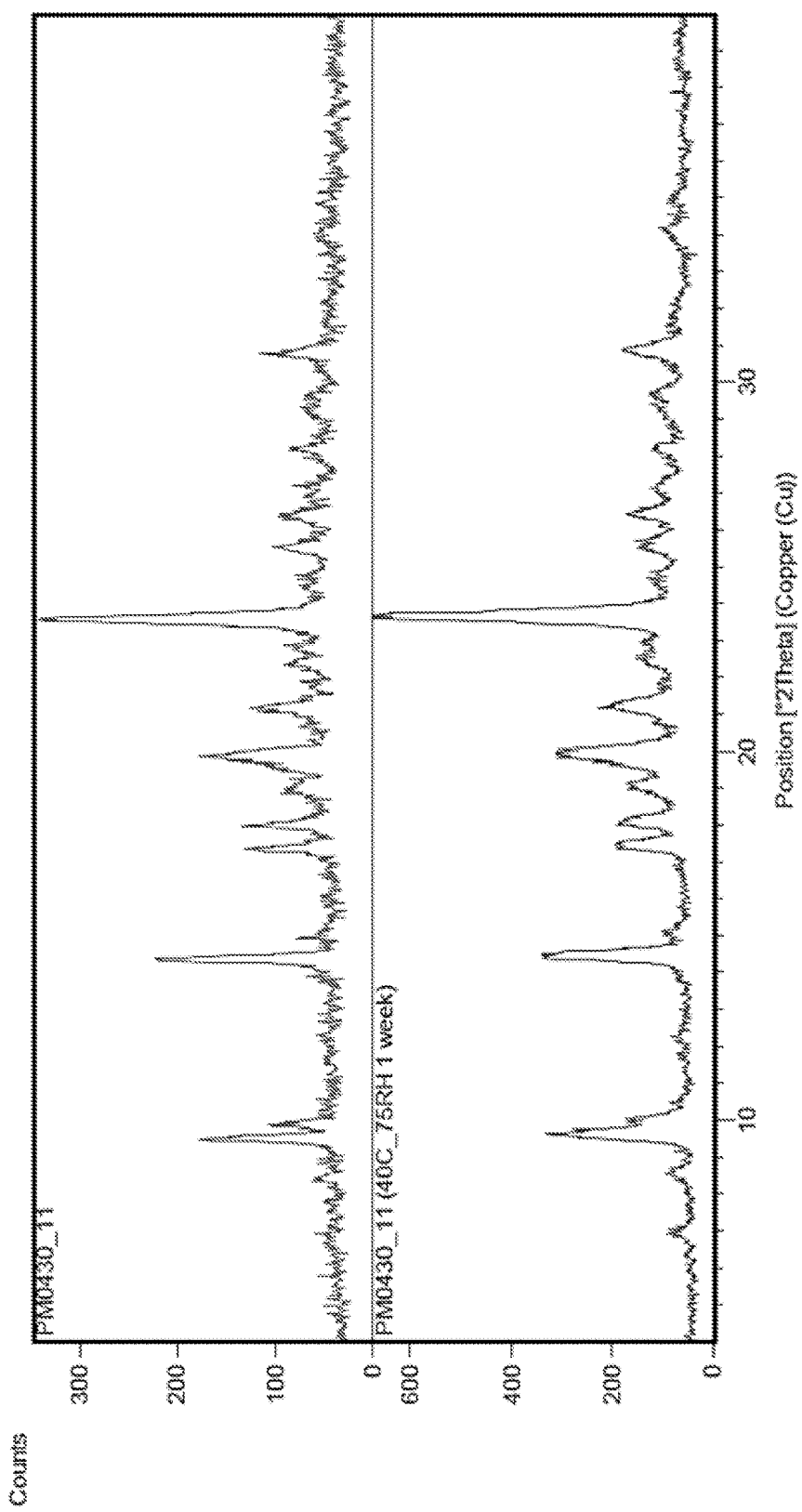
FIG. 7 is XRPD overlay polymorph Form A of Compound I at 40° C./75% RH T=0 (top) vs T=7 days.
Figure 8:
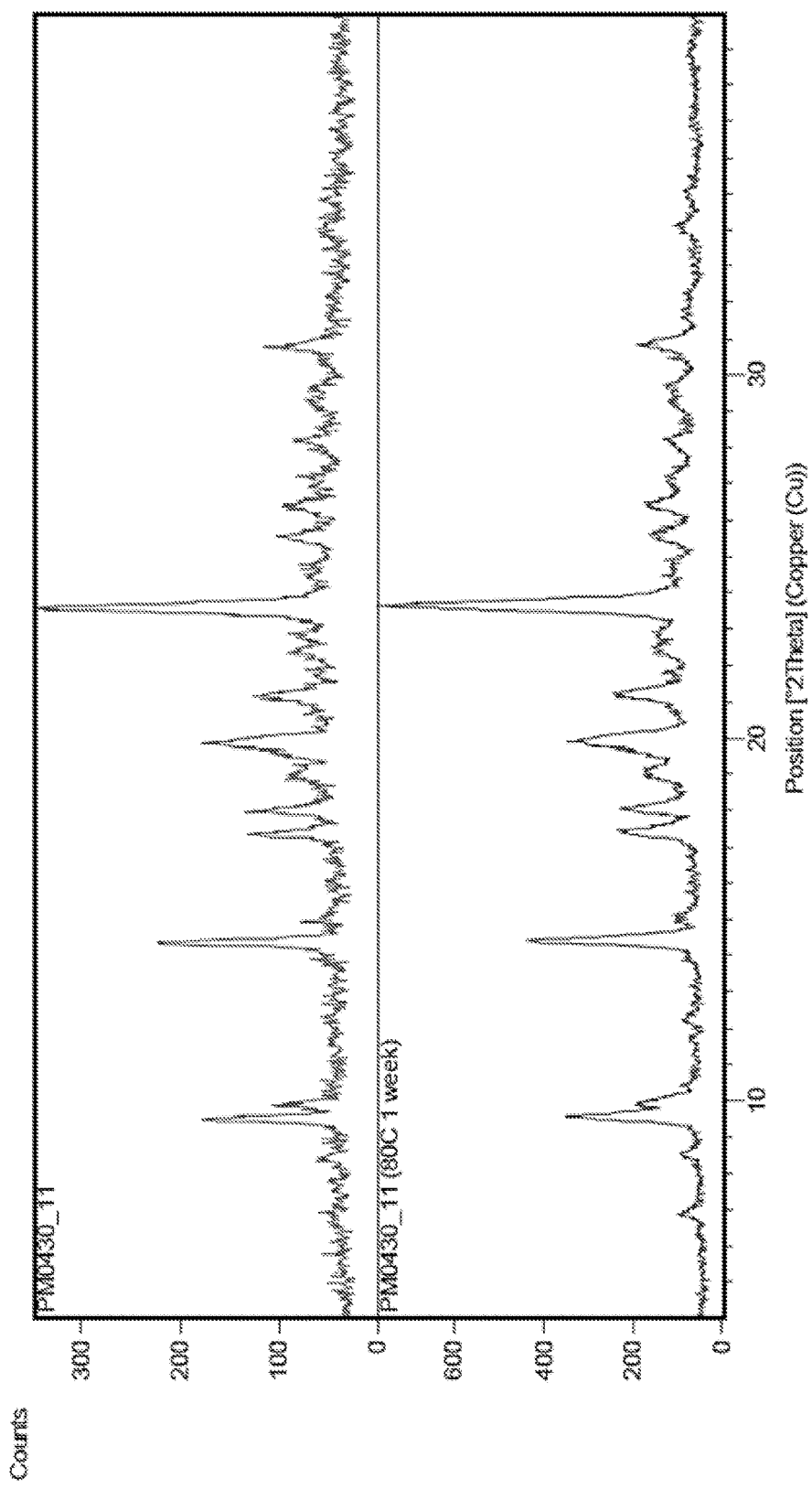
FIG. 8 is XRPD overlay polymorph Form A of Compound I at 80° C. T=0 (top) vs T=7 days.
Figure 10:
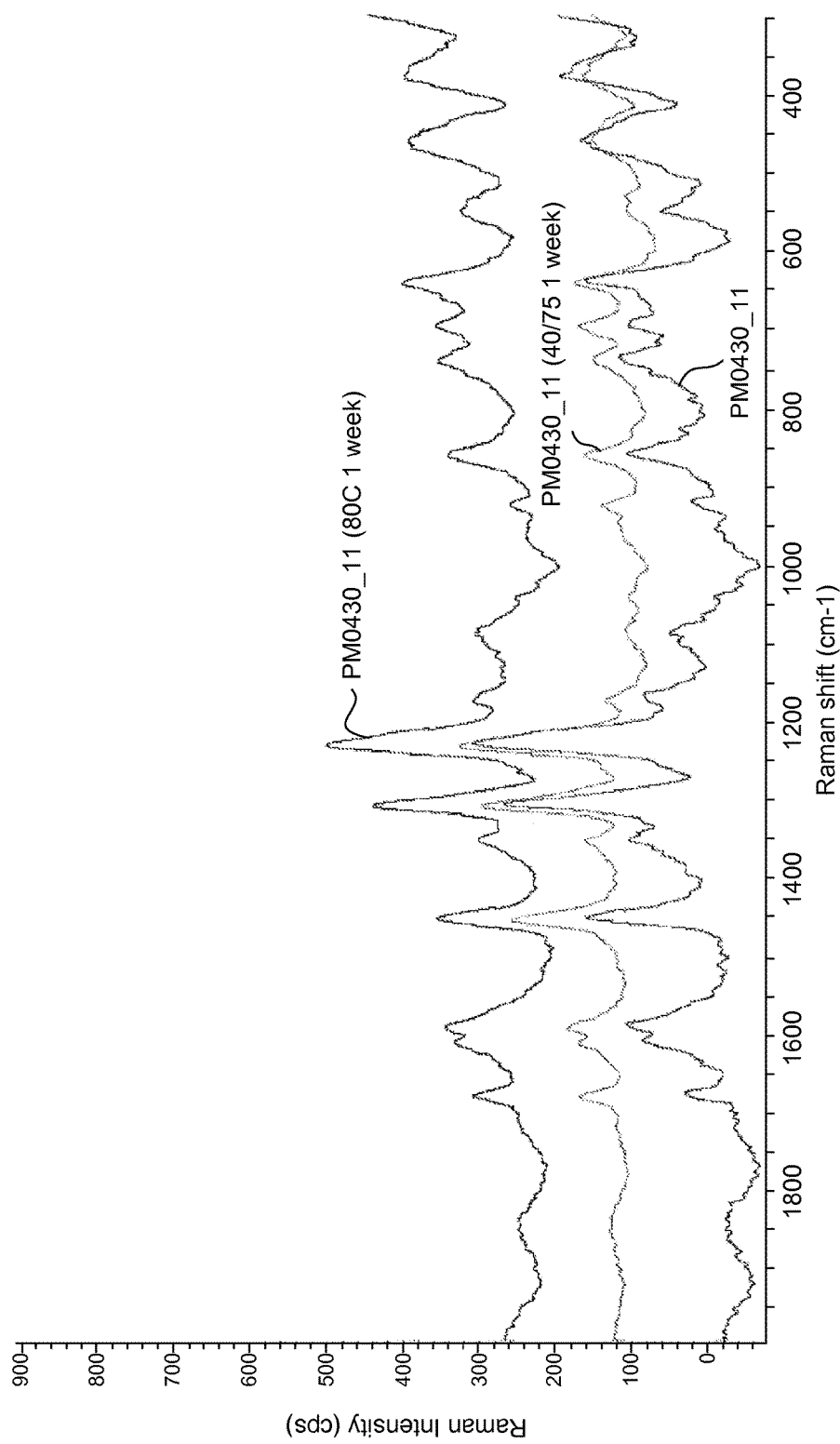
FIG. 10 is Raman spectra overlay of the polymorph Form A of Compound I at T=0 (bottom) vs T=7 days (middle, 40° C./75% RH) and T=7 days (top, 80° C.).

Accelerated stability tests of Compound I at 40° C./75% RH and 80° C. detected no instability as measured by XRPD and Raman over 1 week, see FIG. 7 and FIG. 8 and FIG. 10. Thus, Form A is a stable polymorphic form which is particularly useful for pharmaceutical compositions.

Figure 6:
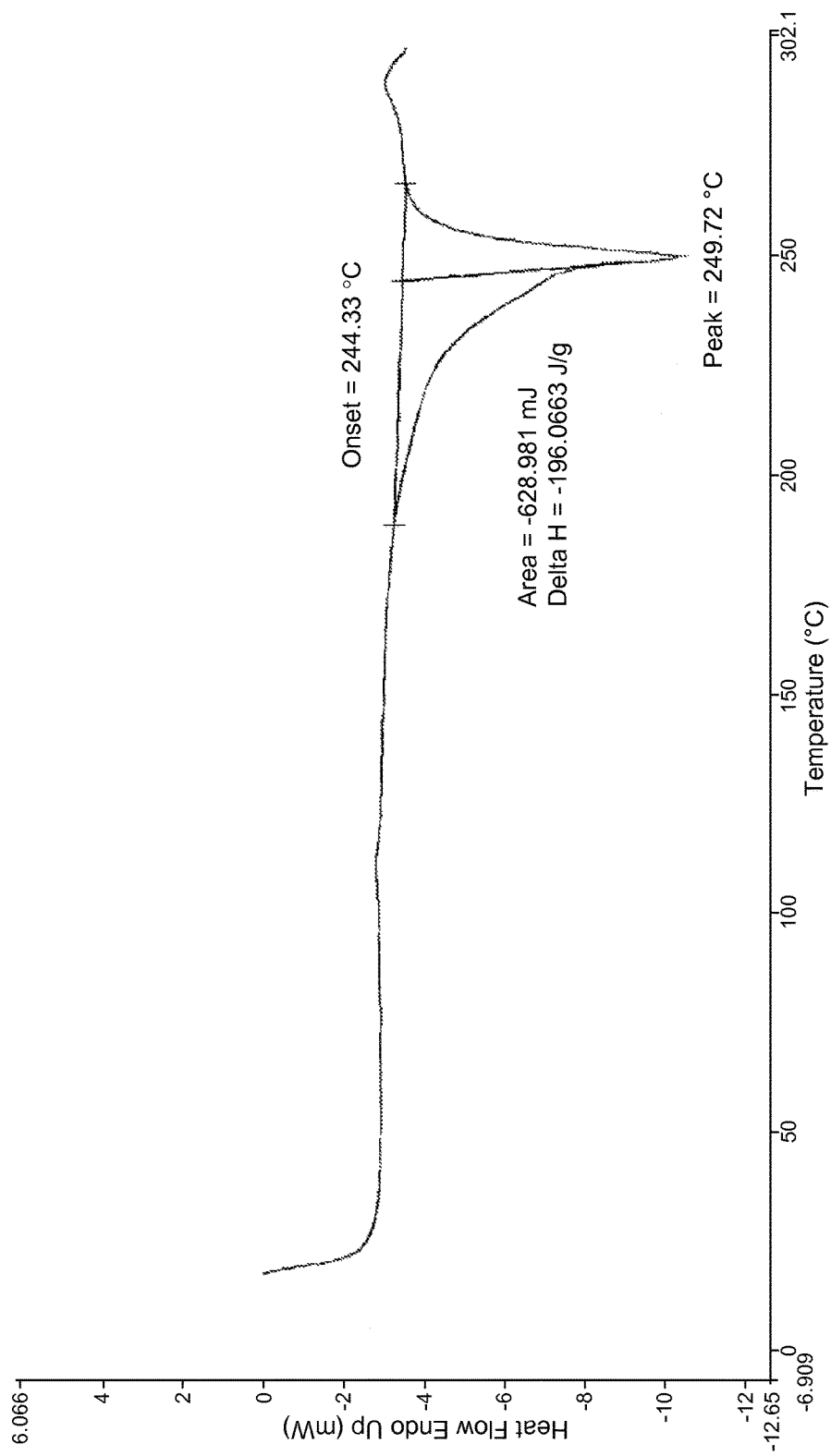
FIG. 6 is Differential Scanning Calorimetry (DSC) spectra of polymorph Form A of Compound I.
Figure 9:
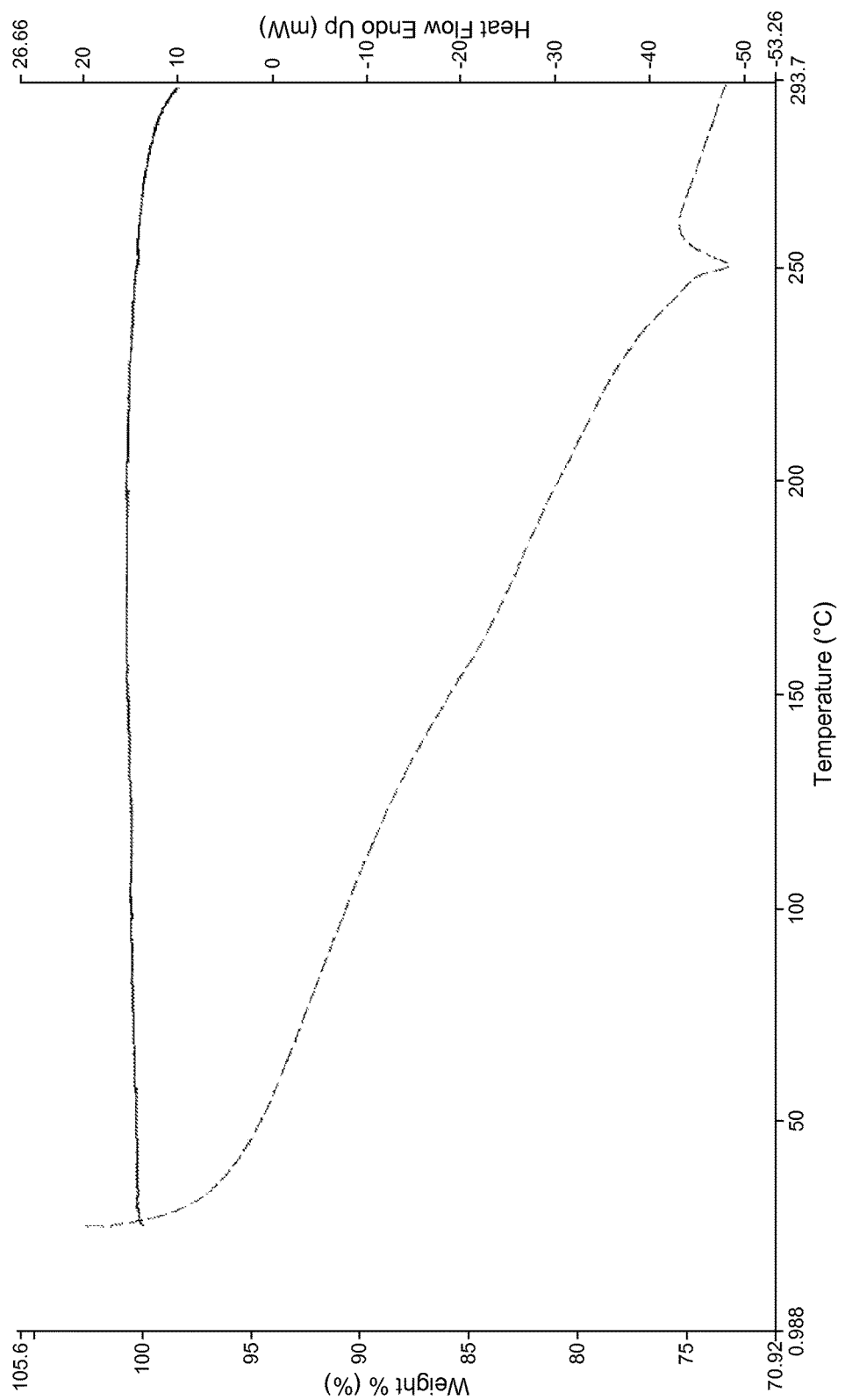
FIG. 9 is STA spectra polymorph Form A of Compound I.

STA data (FIG. 9) indicated the Compound I was not hydrated or solvated. The DSC data did not indicate a clear melt up to about 200° C., as shown in FIG. 6.

Form B was prepared by using slurry method from either amorphous Compound I or other polymorphic forms with solvent of ethanol:water (9:1), which was followed by drying under reduced pressure and ambient temperature.

Form C was prepared by using slurry method from either amorphous Compound I or other polymorphic forms with solvent of THF:water (7:3), which was followed by drying under reduced pressure and ambient temperature.

Form D was prepared by using methanol recrystallization process from either amorphous Compound I or other polymorphic forms, which was followed by drying under reduced pressure and ambient temperature.

Form E was prepared from either amorphous Compound I or other polymorphic forms by using slurry with the compound of Formula I in 0.1 M NaOH/methanol solution, followed by washing with MTBE, which was followed by air dry.

Figure 16:
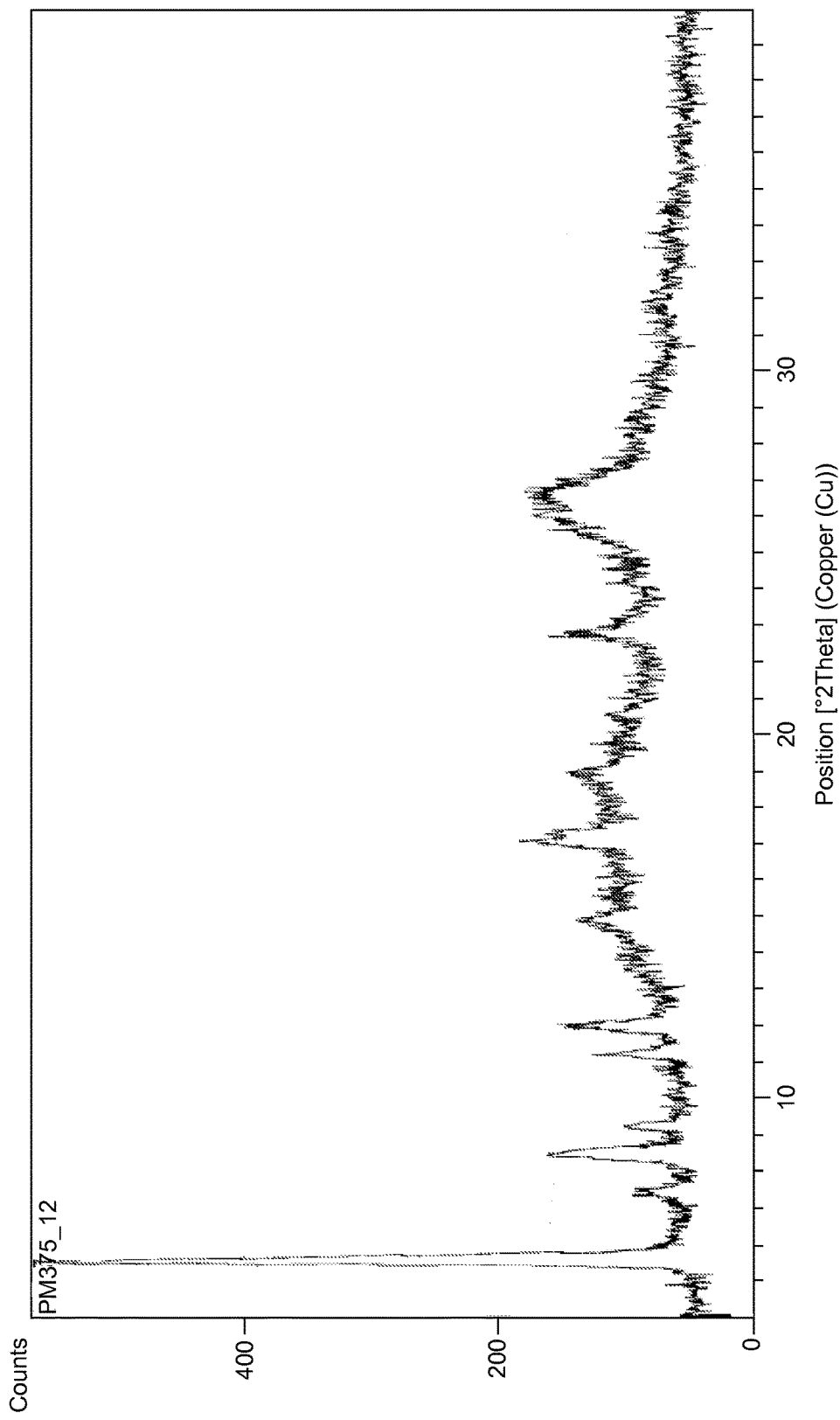
FIG. 16 is X-ray powder diffraction (XRPD) spectra of the polymorphic form, Form D of Compound I.

Form D of the compound of Compound I can have an XRPD spectrum as shown in FIG. 16, for example, with one or more, three or more, five or more, seven or more, ten or more, or all of the peaks shown in Table 2.

TABLE 2

XRPD Table of the polymorphic form, Form D of Compound I

| No. | Pos. [°2Th.] | Rel. Int. [%] |
|---|---|---|
| 1 | 5.58 | 100 |
| 2 | 7.43 | 6.5 |
| 3 | 8.45 | 18.72 |
| 4 | 9.21 | 8.1 |
| 5 | 11.23 | 7.01 |
| 6 | 11.98 | 14.09 |
| 7 | 14.86 | 19.3 |
| 8 | 17.02 | 28.9 |
| 9 | 18.91 | 15.09 |
| 10 | 22.80 | 9.52 |
| 11 | 26.03 | 91.9 |
| 12 | 26.72 | 54.72 |

Figure 17:
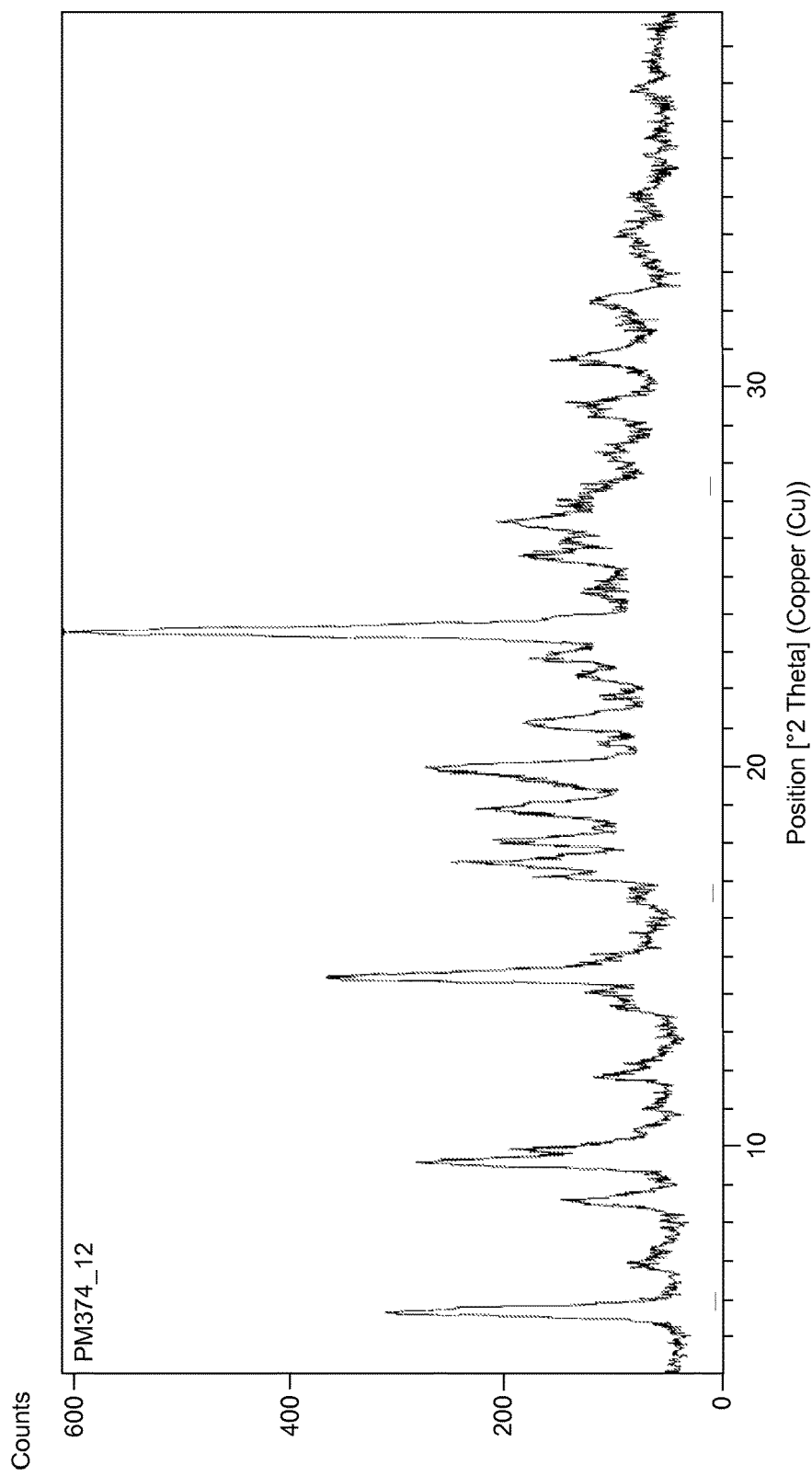
FIG. 17 is X-ray powder diffraction (XRPD) spectra of the polymorphic form, Form E of Formula I compound.

In another aspect, the present invention comprises another crystalline form (Form E) of the Formula I compound described above. Form E can exhibit an XRPD pattern with peaks at one or more of 5.6±0.3, 6.8±0.3, 8.6±0.3, 9.5±0.3, 11.8±0.3, 14.4±0.3, 17.1±0.3, 17.4±0.3, 18.0±0.3, 18.9±0.3, 20.0±0.3, 21.0±0.3, 22.3±0.3, 23.5±0.3, 25.5±0.3, 26.4±0.3, 28.3±0.3, 29.6±0.3, 30.7±0.3, 32.3±0.3, and 34.0±0.3 degrees 2-theta, such as the XRPD peaks described in Table 3. FIG. 17 shows an XRPD diffraction pattern of Form E.

TABLE 3

| No. | Pos. [°2Th.] | Rel. Int. [%] |
|---|---|---|
| 1 | 5.5698 | 65.4 |
| 2 | 6.8459 | 9.97 |
| 3 | 8.5515 | 23.62 |
| 4 | 9.5049 | 59.91 |
| 5 | 11.7857 | 11.04 |
| 6 | 14.3744 | 99 |
| 7 | 17.0602 | 17.22 |
| 8 | 17.4307 | 35.68 |
| 9 | 18.0062 | 34.51 |
| 10 | 18.8925 | 62.85 |
| 11 | 19.9711 | 74.64 |
| 12 | 21.0152 | 41.12 |
| 13 | 22.3471 | 26.86 |
| 14 | 22.8398 | 26.95 |
| 15 | 23.5282 | 100 |
| 16 | 25.496 | 34.92 |
| 17 | 26.3928 | 46.46 |
| 18 | 28.264 | 22.95 |
| 19 | 29.5631 | 16.22 |
| 20 | 30.7097 | 28.12 |
| 21 | 32.2629 | 25.41 |
| 22 | 34.0447 | 16.24 |
| 23 | 37.8132 | 7.49 |

To prepare a pharmaceutical composition containing the active substance, particularly an orally administered pharmaceutical composition, most preferably a tablet, procedures known in the art may be used. For example, tablets can be prepared according to the formulations and methods discussed in *Remington: The Science and Practice of Pharmacy*, which is hereby incorporated by reference for all purposes. Suitable tablets may be obtained, for example, by mixing the active substance(s) with known excipients, for example, inert diluents such as mannitol, sorbitol, xylitol, saccharose, calcium carbonate, calcium phosphate, or lactose, disintegrants such as croscarmellose sodium salt (cellulose carboxymethylether sodium salt, cross-linked), crospovidone, sodium starch glycolate, hydroxypropylcellulose (low-substituted), or maize starch, binders such as polyvinylpyrrolidone, copolymers of vinylpyrrolidone with other vinyl derivatives (copovidone), hydroxypropylcellulose, hydroxypropylmethylcellulose, microcrystalline cellulose, or starch, lubricants such as magnesium stearate, sodium stearyl fumarate, or talc and/or agents for obtaining delayed release, such as hydroxypropylmethylcellulose, carboxymethylcellulose, cellulose acetate phthalate, or polyvinyl acetate. The tablets may also comprise several layers. The following are some examples of pharmaceutical preparations which may be used according to the invention. They are intended purely as illustrations by way of example without restricting the subject matter of the invention thereto. All of the present crystalline polymorphs, i.e., Forms A, B, C, D, and E, can be used for pharmaceutical compositions as exemplified in the formulation examples below.

Formulation Example 1

| Tablet 1 | |
|---|---|
| Ingredients | mg |
| Compound I | 83.417 |
| Mannitol | 299.083 |
| Macrocrystalline cellulose | 100.000 |
| Croscarmellose sodium salt | 10.000 |
| Magnesium stearate | 7.500 |
| Total | 500.000 |

Formulation Example 2

| Tablet 2 | |
|---|---|
| Ingredients | mg |
| Compound I | 83.417 |
| Sorbitol | 384.083 |
| Povidone K25 | 25.000 |
| Magnesium stearate | 7.500 |
| Total | 500.000 |

Formulation Example 3

| Tablet 3 | |
|---|---|
| Ingredients | mg |
| Compound I | 41.708 |
| Mannitol | 149.542 |
| Microcrystalline cellulose | 50.000 |
| Croscarmellose sodium salt | 5.000 |
| Magnesium stearate | 3.750 |
| Total | 250.000 |

Formulation Example 4

By directly compressing the Compound I with the excipients sorbitol and magnesium stearate, tablets are obtained whose concentration of active substance corresponds to an amount of 80 mg, 40 mg, and 20 mg of free acid of Compound I.

| Tablet containing the Equivalent of 80 mg of Free Acid of Compound I. | | |
|---|---|---|
| Ingredient | mg/tablet | % Tablet |
| Compound I | 83.417 | 17.379 |
| Sorbitol | 389.383 | 81.121 |
| Magnesium stearate | 7.2 | 1.5 |
| Total | 480 | 100 |

| Tablet containing the Equivalent of 40 mg of Free Acid of Compound I. | | |
|---|---|---|
| Ingredient | mg/tablet | % Tablet |
| Compound I | 41.708 | 17.378 |
| Sorbitol | 194.692 | 81.122 |
| Magnesium stearate | 3.6 | 1.5 |
| Total | 240 | 100 |

| Tablet containing the Equivalent of 20 mg of Free Acid of Compound I. | | |
|---|---|---|
| Ingredient | mg/tablet | % Tablet |
| Compound I | 20.854 | 17.378 |
| Sorbitol | 97.346 | 81.122 |
| Magnesium stearate | 1.8 | 1.5 |
| Total | 120 | 100 |

Formulation Example 5

The Compound I is first mixed with mannitol, red iron oxide and hydroxypropylcellulose in an intensive mixer. Then magnesium stearate is added by sifting through a 0.8 mm screen and the mixture is subjected to dry granulation in a roller compactor. In parallel, hydrochlorothiazide is mixed with mannitol, microcrystalline cellulose, sodium glycol starch, and red iron oxide in an intensive mixer. Both this mixture and the granulated Compound I are sieved through a 0.8 mm screen, mixed together in a free fall blender, and finally subjected to a last mixing process with magnesium stearate screened through a 0.8 mm screen. A composition is obtained which can be compressed without any problems and the tablets produced from it exhibit good solubility for the active substances. This composition of active substances and excipients is compressed with a suitable tablet press. Tablets of the following composition are prepared, the amount of Compound I contained in each tablet corresponding to an amount of 80 mg of the free acid of Compound I.

| Ingredient | mg/tablet | % Tablet |
|---|---|---|
| Compound I | 83.417 | 13.903 |
| Hydrochlorothiazide | 12.500 | 2.083 |
| Mannitol | 336.483 | 56.081 |
| Cellulose microcrystalline | 120.000 | 20.000 |
| Sodium glycol starch | 30.000 | 5.000 |
| Red iron oxide | 0.600 | 0.100 |
| Hydroxypropylcellulose | 5.000 | 0.833 |
| Magnesium stearate | 12.000 | 2.000 |
| Total | 600 | 100 |

The composition of the tablet may also be as follows:

| Ingredient | mg/tablet | % Tablet | %/Granules |
|---|---|---|---|
| Compound I | 83.417 | 13.903 | 83.417 |
| Mannitol | 10.983 | 1.831 | 10.983 |
| Hydroxypropylcellulose | 5.000 | 0.833 | 5.000 |
| Red iron oxide | 0.100 | 0.017 | 0.100 |
| Magnesium stearate | 0.500 | 0.083 | 0.500 |
| Total | 100.000 | 16.667 | 100.000 |
| Hydrochlorothiazide | 12.500 | 2.083 | |
| Mannitol | 325.500 | 54.250 | |

-continued

| Ingredient | mg/tablet | % Tablet | %/Granules |
|---|---|---|---|
| Cellulose microcrystalline | 120.000 | 20.000 | |
| Sodium glycol starch | 30.000 | 5.000 | |
| Red iron oxide | 0.500 | 0.083 | |
| Magnesium stearate | 11.500 | 1.917 | |
| Total | 600.000 | 100.000 | |

Formulation Example 6

Hydrochlorothiazide, Compound I, sorbitol, and red iron oxide are mixed in a free fall blender, passed through a 0.8 mm screen and, after the addition of magnesium stearate, processed in a free fall blender to form a powdered mixture. This composition of active substances and excipients is then compressed into tablets using a suitable tablet press. Tablets of the following composition are prepared, the amount of Compound I contained in each tablet corresponding to an amount of 80 mg of the free acid of Compound I.

| Ingredient | Mg/tablet | % Tablet |
|---|---|---|
| Compound I | 83.417 | 13.903 |
| Hydrochlorothiazide | 12.500 | 2.083 |
| Sorbitol | 494.483 | 82.414 |
| Red iron oxide | 0.600 | 0.100 |
| Magnesium stearate | 9.000 | 1.500 |
| Total | 600.000 | 100.000 |

Formulation Example 7

Capsule Containing the Equivalent of 100 mg of Free Acid of Compound I.

| Ingredients | mg |
|---|---|
| Compound I | 100 |
| Cellulose microcrystalline | 170 |
| Total | 270 |

X-ray Powder Diffraction (XRPD).

Approximately 2 mg of sample was gently compressed on the XRPD zero back ground single obliquely cut silica sample holder. The sample was then loaded into a D/MAX 2200 X-ray powder diffractometer (Rigaku) or a Philips X-Pert MPD diffractometer and analyzed using the following experimental conditions (Tube anode: Cu; Generator tension: 40 kV; Tube current: 40 mA; Wavelength alpha1: 1.54056 Å; Wavelength alpha2: 1.5444 Å; Start angle [2 theta]: 5; End angle [2 theta]: 50; and Continuous scan). For suspected novel forms a slightly slower scan speed was used over a range of 4-40029.

It is known in the art that for the same sample or test article measured by different X-ray powder diffractometers or, even by the same X-ray powder diffractometer but measured at different times or temperature or conditions, the values of peak positions at degree two-theta may have about ±0.3 or ±0.5 variations.

Raman Spectroscopy.

Samples were analyzed by a Nicolet Almega XR Dispersive Raman Microscope for its Raman spectrum using the following conditions (Exposure Time: 1.0 s; Acquisition No: 10; Pinhole Size: 25, 50 or 100 am; Wavelength range: 2000~300 $cm^{-1}$ (single grating); Laser: He—Ne 780 nm 100% power, Objective: 20×/0.40 or 50×/0.75 (magnifier/numerical aperture number)). Then the measured Raman spectra were corrected by baseline subtraction using the software OMNIC™ v7.3.

Simultaneous Thermal Analysis (STA).

Approximately 5 mg of sample was accurately weighed into a ceramic crucible and it was placed into the chamber of Perkin-Elmer STA 600 TGA/DTA analyzer at ambient temperature. The sample was then heated at a rate of 10° C./min from 25° C. to 300° C. during which time the change in weight was monitored as well as DTA signal. The purge gas used was nitrogen at a flow rate of 20 $cm^3$/min.

Differential Scanning Calorimetry (DSC).

Approximately, 5 mg of each sample was weighed into an aluminum DSC pan and sealed non-hermetically with an aluminum lid. The sample was then loaded into a Perkin-Elmer Jade DSC and held at 25° C. Once a stable heat-flow response was obtained, the sample was then heated to 300° C. at a scan rate of 10° C./min and the resulting heat flow response was monitored. A 20 $cm^3$/min helium purge was used. Prior to analysis, the instrument was temperature and heat flow verified using an indium standard.

Polarised Light Microscopy (PLM).

An Olympus BX50 microscope, equipped with an analyser and polariser, was used to observe each sample under polarised light. Micrographs of the sample were taken by using a JVC-TKC1380 digital camera connected to a PC running Studio QuickStart version 9.3.2. A 20×/0.5 (magnifier/numerical aperture (NA) value) objective was used to view samples and capture images.

Gravimetric Vapor Sorption (GVS).

Approximately 20 mg of sample was placed into a wire-mesh vapor sorption balance pan and loaded into an 'IgaSorp' vapor sorption balance (Hiden Analytical Instruments). The sample was then dried by maintaining a 0% humidity environment until no further weight change was recorded. Subsequently, the sample was then subjected to a ramping profile from 0-90% RH at 10% RH increments, maintaining the sample at each step until equilibration had been attained (99% step completion). Upon reaching equilibration, the % RH within the apparatus was ramped to the next step and the equilibration procedure repeated. After completion of the sorption cycle, the sample was then dried using the same procedure. The weight change during the sorption/desorption cycles were then monitored, allowing for the hygroscopic nature of the sample to be determined.

BIOLOGICAL ACTIVITIES

Rat Pharmacokinetics.

Compound I was dosed to nonfasted male CD IGS rats (weighting 180-250 g, Charles River Laboratories) by single intravenous (IV, n=3/group) or oral gavage (PO, n=4/group, including control rat group for drug-free blood and brain collection) administration at a nominal dose levels of 3 mg/kg (IV) or 5 mg/kg (IV) and 10, 50, 100 mg/kg (PO) respectively. Compound was formulated in either DMSO/Solutol: HS 15/phosphate buffered saline, pH 7.4 (PBS) for both IV and PO dosing, or 10% (w/v) Povidone K12 in water for IV dosing or 10% (w/v) Povidone K25 in water for PO dosing, or 18% (w/v) CrosPovidone in water for PO dosing. An intravenous profile was obtained by taking serial or terminal blood samples at 3, 10, 30, 60, 120, 240, 360, 1440 min post dose. An oral profile was obtained by taking serial or terminal blood samples at 10, 30, 60, 120, 240, 360, 480, 1440 min post dose.

Plasma Sample Collection from Rats. Animals were sedated under general inhalant anesthesia (3% isoflurane) for blood collection by cardiac puncture. Blood aliquots (300-400 μL) were collected in tubes coated with lithium heparin, mixed gently, then kept on ice and centrifuged at 2,500×g for 15 minutes at 4° C., within 1 hour of collection. For control animals, blood was collected by cardiac puncture. The plasma was then harvested and kept frozen at −20° C. until further processing.

Plasma Sample Collection from Cannulated Rats.

Blood collection was carried out from the jugular vein catheter. Blood aliquots (300-400 μL) were collected in tubes coated with lithium heparin, mixed gently, then kept on ice and centrifuged at 2,500×g for 15 minutes at 4° C., within 1 hour of collection. For control animals, blood was collected by cardiac puncture. The plasma was then harvested and kept frozen at −20° C. until further processing.

Brain Sample Collection from Rats.

Immediately after the blood sampling, rats were decapitated and the whole brains were quickly removed, rinsed with cold saline (0.9% NaCl, g/mL), surface vasculature ruptured, blotted with dry gauze, weighed and kept on ice until further processing within 1 hour of collection. Each brain was homogenized in 3 mL cold phosphate-buffered saline, pH 7.4 for 10 seconds on ice using Power Gen 125. The brain homogenate from each brain was then stored at −20° C. until further processing.

Plasma and brain samples were subjected to quantitative analysis by LC-MS/MS using compound-specific mass transitions. Drug concentration-time profiles were generated and non-compartmental PK analysis (using WinNonlin) used to generate estimates of half-life ($T_{1/2}$), clearance, volume of distribution ($V_{ss}$), and oral bioavailability (F %) (Gabriesson, J. and Weiner, D. Pharmacokinetic and Pharmacodynamic Data Analysis: Concepts and Applications. Swedish Pharmaceutical Press, 1997). The concentrations of the test compound in brain (ng/g brain tissue) and in plasma (ng/mL) as well as the ratio of the brain concentration and the plasma concentration at each time point were determined and reported.

For Compound I, the mean pharmacokinetic parameters are determined as following:

| Dose (mg/kg) | Route | F (%) | $C_{max}$ (ng/mL) | $T_{1/2}$ (min) | Clearance (mL/min/kg) | $V_{ss}$ (mL/kg) |
|---|---|---|---|---|---|---|
| 3 | IV | | | 65 | 4 | 287 |
| 100 | PO | ~100 | 66008 | 124 | | |

| Dose (mg/kg) | Route | Dose (mg/kg) | Time (min) | Brain concentration (ng/g brain) | Plasma Concentration (ng/mL) | Ratio Brain/Plasma (mL/g brain) |
|---|---|---|---|---|---|---|
| 3 | IV | 5 | 30 | 153 | 11279 | 1.4% |
| 3 | IV | 5 | 60 | 120 | 8161 | 1.8% |
| 3 | IV | 5 | 180 | 23 | 1833 | 1.9% |

Compound Inhibition in a Live, Whole Cell Based Functional Assay:

There are several methods to measure whole length TrkA activation stimulated by its natural ligand or agonist NGF in live cells. For example, the PathHunter Profiling services offered by DiscoveRx (Fremont, Calif.). The PathHunter technology is an adaptation of enzyme fragment complementation that provides a novel, generic functional cell-based assay format for detecting protein-protein interactions. In this cell-based assay approach, with U2OS cell background, a small peptide epitope (PK) is expressed recombinantly on the intracellular C-terminus of TrkA (human full length). This is co-expressed with a larger sequence, termed enzyme acceptor (EA) that is attached to a cytoplasmic protein SHC1 which will interact with TrkA intracellularly. NGF induced activation of TrkA receptor causes either homo- or hetero-dimerization of TrkA resulting in cross-phosphorylation. The SHC1-EA fusion protein then binds the phosphorylated TrkA receptor forcing complementation of the PK and EA fragment. This interaction generates an active beta-galactosidase enzyme, which is detected using a chemiluminescent substrate. In such cell-based functional assays, the Compound I of the present invention inhibits NGF stimulated TrkA activation at low nanomolar concentration (cellular $IC_{50}$ is about 50 nM, mean of triplicate), while virtually has no effect on either BDNF stimulated TrkB, or NT3 stimulated TrkC activation ($IC_{50}$ more than 10,000 nM in both cases, triplicate, with a positive control compound of pan-kinase inhibitor, staurosporine or K-252a, an internal agonist control and a negative control compound).

Cell Viability and Proliferation Assays.

To assess the chemosensitivity of tumor cells, cell viability is measured by CellTiter-Glo® Luminescent Cell Viability Assay (Promega; WI, USA) per the manufacturer's instruction. Briefly, 5×103 to 7×105 cells/ml are cultured in sterile 96-well plates in the presence of increasing concentrations of the drugs (test article, 0 to 100 μM), or vehicle in RPMI medium. The plates are then incubated for 24 to 96 h, and then 100 μl of CellTiter-Glo reagent is added to lyse the cells. After a 10-min incubation at room temperature, the luminescence is recorded in a luminometer with an integration time of 1 s per well. The luminescence signals for the drug-treated cells are normalized by the luminescence signal obtained from vehicle-treated cells. As an alternative method to quantitate cell viability, the trypan blue exclusion dye method was used. Vehicle- or drug-treated cells were assayed by adding trypan blue solution (0.4% in phosphate-buffered saline [PBS]) to the culture medium. After 3 min, the number of dead cells that retained the dye is compared to the total number of cells to calculate cell viability. GraphPad Prism 5 software is used to calculate IC50 and plot effect-dose curve of drugs. Multiplate reader: EnVision 2104 (PerkinElmer). % of control variability=100*[(X (drug_treated)−L(baseline))/(H(vehicle_control)−L(baseline))]. Such assays show that for example, Compound I, has IC50 value about 2 to 5 μM in human pancreatic cancer cells (from ATCC) of AsPC-1. MIA PaCa-2, BxPC-3, Capan-1 and Panc-1; about 2 to 8 μM in human liver cancer cells of SK-HEP-1 and HepG2; and about 7 μM in human stomach cancer cells of NCI-N87, after 24 h or 48 h or 96 h incubation. Taxol, erlotinib, sorafenib and gemcitabine are used as controls, and the compounds of present inventions are synergistic or additive with gemcitabine, taxol, erlotinib or sorafenib in pancreatic or liver cancer cells.

Rat CFA-Induced Inflammatory Pain Model.

Hyperalgesia was induced by subcutaneously injecting 50 μL of CFA (Sigma-Aldrich, St. Louis, Mo., USA) into the plantar surface of the left hind paw of the rats using a 30-gauge hypodermic needle under sevoflurane anesthesia. The classical signs of inflammation, including edema and redness, for up the last day of tests were recorded. To assess the effect of test article on CFA-induced inflammatory pain, the rats were anesthetized with sevoflurane 3 hours after CFA injection and then injected 50 µL of either 1 mM test article (n=6) or Saline (n=4) subcutaneously (S.C.) into the same site as the CFA injection, using a 30-gauge hypodermic needle under sevoflurane anesthesia, according to published method (Ueda K., et al, *J Pharmacol. Sci.,* 2010; 112(4): 438-43). Paw withdrawal latencies (thermal hyperalgesia) are measured before and at 2 and 4 and 2, 4, and 7 days after CFA injection. Mechanical thresholds were also measured in the same way with either Formula 1 compound (n=6) or Saline (n=4) at similar different time points (for example, 1, 3 hour and 3 days). The noxious heat and mechanical thresholds were separately measured in each group of rats. The threshold was measured 3-5 times in each rat and then averaged. Stimulus interval was 5 min. The analgesic effect of Compound I on this rat CFA-induced inflammatory pain model is given in FIG. 1, where it clearly shown that Compound I is efficacious in relieving the pain in this rat pain model.

Chronic Constriction Injury (CCI) Model of Neuropathic Pain in Rat.

The CCI model is one of the most commonly used mono-neuropathic pain model firstly described in details by Bennett and Xie (Bennett G J, Xie Y K. Pain. 1988; 33(1):87-107). It mimics important clinical chronic pain symptoms such as mechanical allodynia and thermal hyperalgesia. Chronic constriction injury of the sciatic nerve was produced by tying four loose ligatures around the left sciatic nerve according to the method of Bennett and Xie. This procedure resulted in tactile allodynia in the left hindpaw. Calibrated von Frey filaments were used to determine the lowest mechanical (tactile) threshold required to evoke a brisk paw withdrawal reflex in the rat hindpaws. Rats were allowed to acclimatize in wire mesh cages for 15-20 min prior to von Frey testing. Assessment of paw withdrawal thresholds (PWTs) using von Frey filaments was undertaken prior to CCI-surgery (pre-surgery baseline on day 0). Before the drug dosing on day 14, the pre-dose baseline was recorded for each rat. Rats were included in the study only if they did not exhibit motor dysfunction (e.g., paw dragging or dropping) and their PWT was below to 4 g. Drug-naïve CCI-rats (n=4-6 per group) were used. The oral (PO) gavage vehicle was either 10% (w/v) Povidone K25 in water for PO dosing, or 18% (w/v) CrosPovidone in water for PO dosing, or 0.5% CMC-Na/0.1% Tween 80 in distilled water for PO dosing. The positive control gabapentin was dissolved in the vehicle and orally given at 100 mg/kg (by oral gavage). Test article was dissolved or suspended in the vehicle and orally given at 25, 50, 100 and 150 mg/kg. Each CCI-rat was administered a single oral dose of test article, gabapentin or vehicle control, 2 hours before assessment of PWT.

Figure 2:
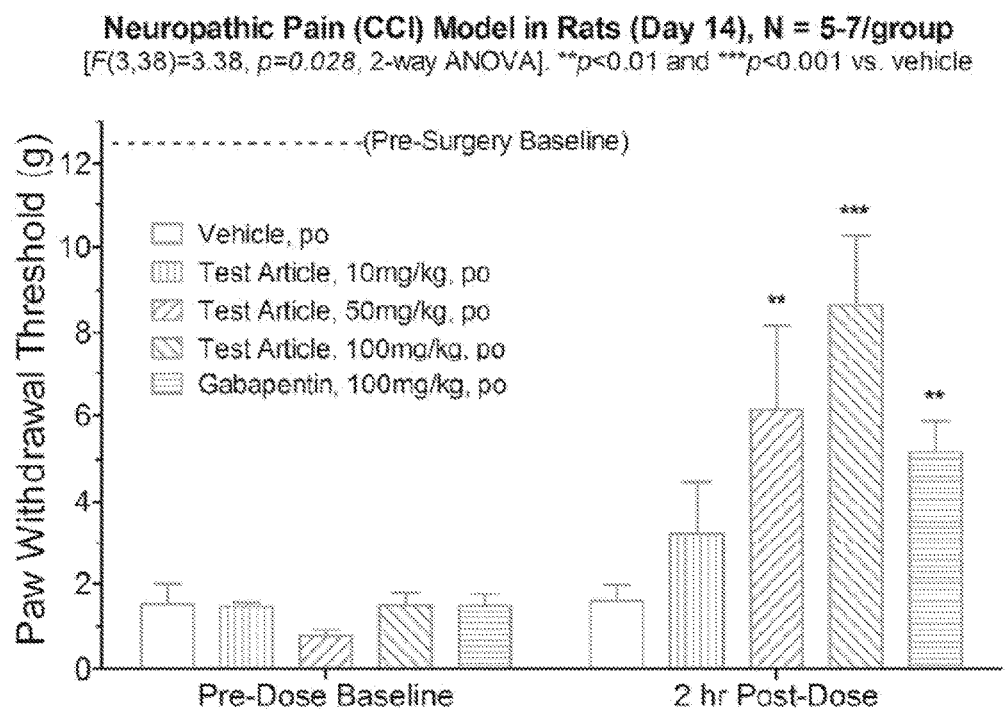
FIG. 2 is a graph showing oral dose-dependent reduction of neuropathic pain of the test article in rat model of neuropathic (CCI) pain.

The results have demonstrated, as shown in FIG. 2, that oral administration of Compound I of present invention significantly reduced mechanical allodynia in CCI rats of neuropathic pain model in a dose-dependent manner. In addition, at the same oral dose of 100 mg/kg, Compound I is about 100% more effective in suppressing mechanical allodynia in CCI neuropathic pain compared to gabapentin, the current gold standard medication for neuropathic pain. Of note, CCI-rats dosed with gabapentin have shown drowsiness or motor incoordination, which is consistent with known side effect of gabapentin. However, no such effect or other abnormality was observed in CCI-rats dosed with Compound I.

Spinal Nerve Ligation (SNL) Mono-Neuropathic Pain Model in Rat.

The surgical procedure will be performed according to the method firstly described by Kim and Chung (Kim S H, Chung J M. Pain. 1992; 50(3):355-63.). This procedure will result in tactile allodynia in the left hindpaw. Rats will be included in the study only if they do not exhibit motor dysfunction (e.g., paw dragging or dropping) and their PWT is below to 4.0 g. The dose-response anti-allodynia effects of test compound: on day 14 after surgery, rats were treated with test article at one of four doses, vehicle or positive control by oral gavage, and PWT was determined by calibrated von Frey filaments at time points of 0 (right before the drug dosing, Pre-Dose Baseline), 0.5, 1, 2, 4 and 6 hr. The anti-allodynia effects of repeated administration of test article: Administration of test article was started on day 7 after surgery, once a day for 7 days. PWT was determined by calibrated von Frey filaments, 2 hour after test article dosing each day. After 7 days dosing, the measurement were continued, every other day without compound dosing for another 7 days. PWT was determined at the time points as given above. The results have demonstrated that oral administration of Compound I of present invention significantly reduced mechanical allodynia in SNL rats of neuropathic pain model in a dose-dependent manner.

Streptozotocin-Induced Diabetic Poly-Neuropathic Pain Model in Rat.

Diabetic peripheral neuropathy is a long-term complication of diabetes mellitus. Rats were received i.p. injections of streptozotocin (STZ, 50 mg/kg dissolved in citrate buffer at pH 4.5 immediately before the injection) to induce insulin-dependent diabetes mellitus and produce tactile allodynia. One week later, blood glucose level was assayed, from samples taken from the tail vein, using standard test strips and colorimeter. Only animals with a blood glucose level >350 mg/dL were considered diabetic and included for the testing. Typical features of neuropathic pain (tactile allodynia) were developed in hindpaws beginning around 2 to 3 weeks after STZ injection. After 4 weeks, a stable level of allodynia was reached. At this point, the rats with PWT below 4.5 g were enrolled for compound testing. The allodynic state was remain intact until the $8^{th}$ week after STZ injection. All animals were observed daily and weighed regularly during the study period. This model of neuropathic pain mimics the symptoms of neuropathy in diabetic patients (Lynch J J, 3rd, et al *Eur J Pharmacol.* 1999; 364(2-3):141-6; Calcutt N A, *J Neurol Sci.* 2004; 220(1-2):137-9). The dose-response anti-allodynia effects of test compound: On day 28 after STZ injection, rats were treated with test compound at one of four doses, or controls (vehicle and positive) by oral gavage, and PWT was determined by calibrated von Frey filaments at time points of 0 (right before the drug dosing, Pre-Dose Baseline), 0.5, 1, 2, 4 and 6 hr. Tolerance effects: 6 days following the day 28 test, i.e. on day 34 after STZ injection, the same procedure on day 28 was repeated on day 34 with the same group of STZ-rats treated with the same (effective) dose as on day 28. The two results of anti-allodynia effects of test compound as measured on day 28 and on day 34 were compared to see if there was any tolerance effect of test compound in animals. The anti-allodynia effects of repeated administration of test compound: Administration (p.o.) of test compound was started on day 21 after STZ injection, once a day for 7 days. PWT was determined by calibrated von Frey filaments once a day, 1 hour after compound dosing. After 7 days dosing, the measurement was continued, every other day without compound dosing for another 7 days. PWT was determined at the time points as given above.

In Vivo Anti-Tumor Effects of Compound I.

Oral administration of Compound I (150 mg/kg) was statistically significant efficacious, for example, with more than 21% tumor volume reduction compared to vehicle treated group (p<0.02), on Day 7 postdose, in subcutaneous xenograft tumor mouse model of human pancreatic cancer cells (PANC-1). The study also showed that Compound I and gemcitabine (40 mg/kg, Q3D) had statistically significant synergistic effects (p<0.01), for example with more than 61% tumor volume reduction compared to vehicle treated group (p<0.01) in the same xenograft mouse model.

Pharmaceutical Compositions of the Disclosure

In one aspect, the present invention provides pharmaceutical compositions comprising one or more compounds of the present invention including the compound having structural Compound I.

The present pharmaceutical compositions contain a therapeutically effective amount of the present invention, preferably in purified form, together with a suitable amount of a pharmaceutically acceptable vehicle, so as to provide a form for proper administration to a patient. When administered to a patient, the present compounds and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration the compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent.

In some embodiments, the present compounds, are formulated in accordance with routine procedures as a pharmaceutical composition adapted for intravenous administration to human beings. Typically, compounds for intravenous administration are solutions in sterile isotonic aqueous buffer. For injection, the present compounds, or salts, solvates, esters, and/or prodrugs thereof, may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the present compounds, are administered by infusion, it can be dispensed, for example, with an infusion bottle containing sterile pharmaceutical grade water or saline. When the present compounds are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compounds may also be formulated in rectal or vaginal pharmaceutical compositions such as suppositories or retention enemas, e.g., containing conventional suppository bases such as cocoa butter or other glycerides.

In addition to the formulations described previously, the present compounds may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example, as an emulsion in an acceptable oil) or ion exchange resins, or as sparingly soluble derivatives, for example, as a sparingly soluble salt.

Therapeutic Doses

The present compound(s), their crystalline form(s) and a pharmaceutically acceptable vehicle is provided, will generally be used in an amount effective to treat or prevent diseases or disorders including: cancer, anxiety, generalized pain disorder, acute pain, chronic pain, inflammatory pain, and neuropathic pain.

The amount of the present compounds that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compounds administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compounds are delivered by oral sustained release administration. Dosing may be repeated intermittently, may be provided alone or in combination with other drugs and may continue as long as required for effective treatment of the disease state or disorder.

Suitable dosage ranges for oral administration to a patient in need depend on the potency of the present compounds, but are generally between about 0.1 mg to about 800 mg of a compound of the invention per kilogram body weight; more preferably, between about 0.01 mg to about 50 mg of a compound of the invention per kilogram body weight; still more preferably, between about 0.05 mg to about 20 mg of a compound of the invention per kilogram body weight; and the patient is an animal; more preferably, a mammal; and most preferably, a human. Dosage ranges may be readily determined by methods known to the artisan of ordinary skill.

Suitable dosage ranges for intravenous (i.v.) administration to a patient in need are about 0.1 mg to about 200 mg per kilogram body weight; more preferably, between about 0.01 mg to about 20 mg of a compound of the invention per kilogram body weight; and the patient is an animal; more preferably, a mammal; and most preferably, a human.

Suitable dosage ranges for intranasal administration to a patient in need are generally about 0.1 mg/kg body weight to about 10 mg/kg body weight; more preferably, between about 0.01 mg to about 1 mg of a compound of the invention per kilogram body weight; and the patient is an animal; more preferably, a mammal; and most preferably, a human.

Suppositories generally contain about 0.1 milligram to about 150 milligrams of a compound of the invention per kilogram body weight and comprise active ingredient in the range of about 0.5% to about 10% by weight.

Recommended dosages for intradermal, intramuscular, intraperitoneal, subcutaneous, epidural, sublingual or intracerebral administration are in the range of about 0.1 mg to about 800 mg per kilogram of body weight; and the patient is an animal; more preferably, a mammal; and most preferably, a human.

Effective doses may be extrapolated from dose-response curves derived from in vitro or animal model test systems. Such animal models and systems are well-known in the art.

The present compounds are preferably assayed in vitro and in vivo, for the desired therapeutic or prophylactic activity, prior to use in humans. For example, in vitro assays can be used to determine whether administration of a specific compound of the invention or a combination of compounds is preferred for reducing the pain or killing the cancer cells. The present compounds may also be demonstrated to be effective and safe using animal model systems.

Preferably, a therapeutically effective dose of the present compounds will provide therapeutic benefit without causing substantial toxicity. Toxicity of the present compounds may be determined using standard pharmaceutical procedures and may be readily ascertained by the skilled artisan. The dose ratio between toxic and therapeutic effect is the therapeutic index. The present compounds generally exhibit particularly high therapeutic indices in treating associated disease and disorders or conditions. The dosage of the present compounds will preferably be within a range of circulating concentrations that include an effective dose with little or no toxicity.

Combination Therapy

In certain embodiments of the present invention, the present compounds can be used in combination therapy with at least one additional active or therapeutic agent. The present compounds and the at least one additional active or therapeutic agent can act additively or, more preferably, synergistically. In some embodiments, the present compounds are administered concurrently, sequentially, or separately with the administration of another therapeutic agent. Exemplary active agents include, but are not limited to, aceglatone, aclarubicin, altretamine, aminoglutethimide; 5-aminogleavulinic acid, amsacrine, anastrozole, ancitabine hydrochloride, 17-1a antibody, antilymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomycin, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b., docetaxel, doxifluridine, doxorubicin hychloride, droloxifene, echinomycin, edatrexate, elliptinium, elmustine, enloplatin, enocitabine, epirubicin hydrochloride, estramustine sodium phosphate, etanidazole, ethoglucid, etoposide, fadrozole hydrochloride, fazarabine, fenretinide, floxuridine, fludarabine phosphate, fluorouracil, flutamide, formestane, fotemustine, gallium nitrate, gencitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithiumn gamolenate, lobaplatin, lomustine, lonidamine, mafosfamide, meiphalan, menogaril, mercaptopurine, methotrexate, methotrexate sodium, miboplatin, miltefosine, misonidazole, mitobronitol, mitoguazone dihydrochioride, mitolactol, mitomycin, mitotane, mitozanetrone hydrochloride, mizoribine, mopidamol, muitlaichilpeptide, muromonabcd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofiran, sobuzoxane, sodium bromebrate, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphine-sulphonate, thioguanine, thioinosine, thiotepa, topotecan, toremifene, treosulfan, trimetrexate, trofosfamide, tumor necrosis factor, ubenimex, uramustine, vinblastine sulphate, vincristine sulphate, vindesine sulphate, vinorelbine tartrate, vorozole, zinostatin, zolimomab aritox, zorubicin hydrochloride, an inhibitor of protein kinase A (PKA) or PKC, an inhibitor of cAMP signaling, a nonsteroidal anti-inflammatory drug, a prostaglandin synthesis inhibitor, a local anesthetic, an anticonvulsant, an antidepressant, an opioid receptor agonist, and a neuroleptic, a benzodiazepine, a barbiturate, a neurosteroid and a inhalation anesthetic, a anesthetic and another pain killer and the like, either individually or in any combination.

INCORPORATION BY REFERENCE

All references, articles, publications, patents, patent publications, and patent applications cited herein are incorporated by reference in their entireties for all purposes.

Specifically, U.S. patent application Ser. No. 14/208,244 and PCT Application No. PCT/US2014/027591, are hereby incorporated by reference in their entirety.

However, mention of any reference, article, publication, patent, patent publication, and patent application cited herein is not, and should not be taken as, an acknowledgment or any form of suggestion that they constitute valid prior art or form part of the common general knowledge in any country in the world.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating pain in a subject in need thereof, comprising administering to the subject a pharmaceutical composition, comprising an effective amount of a crystalline polymorph of Compound I, sodium 4-((3-(4-cyclohexylpiperazin-1-yl)-6-oxo-6H-anthra[1,9-cd]isoxazol-5-yl)amino)benzoate, with the following structure:

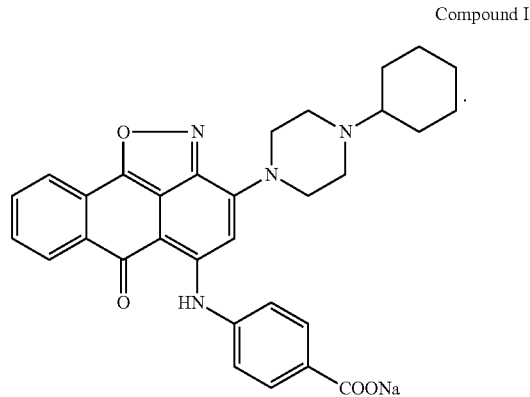

Compound I having Form A, Form B, Form C, Form D, or Form E, wherein:

Form A is characterized by having x-ray powder diffraction pattern peak positions at degree two-theta of 10.0±0.3, 20.1±0.3, and 23.6±0.3;

Form B is characterized as having an x-ray powder diffraction pattern exhibiting three or more peak positions at a degree two-theta selected from the group consisting of about: 9.8±0.3, 10.2±0.3, 14.5±0.3, 17.8±0.3, 18.5±0.3, 19.6±0.3, 21.0±0.3, 21.7±0.3, 23.1±0.3, 25.0±0.3, 25.6±0.3, 28.4±0.3, 29.4±0.3, 30.2±0.3, and 31.6±0.3;

Form C is characterized as having an x-ray powder diffraction pattern exhibiting three or more peak positions at a degree two-theta selected from the group consisting of about: 9.0±0.3, 9.8±0.3, 10.2±0.3, 14.3±0.3, 15.9±0.3, 17.4±0.3, 18.2±0.3, 18.9±0.3, 19.2±0.3, 19.6±0.3, 20.2±0.3, 21.3±0.3, 22.1±0.3, 22.7±0.3, 24.7±0.3, 28.3±0.3, 28.9±0.3, 29.1±0.3, and 30.1±0.3;

Form D is characterized as having an x-ray powder diffraction pattern peak positions at a degree two-theta of about: 5.6±0.3, 26.0±0.3, and 26.7±0.3; and Form E is characterized as having an x-ray powder diffraction pattern peak positions at a degree two-theta of about: 14.4±0.3, 20.0±0.3 and 23.5±0.3, wherein the crystalline polymorph of Compound I is formulated in the pharmaceutical composition in a unit dosage form adapted for intraosseous or intra-articular administration.

2. The method of claim 1, wherein the pain is selected from the group consisting of cancer pain and osteoarthritis pain.

3. The method of claim 1, the crystalline polymorph of Compound I having Form A.

4. The method of claim 3, wherein the crystalline polymorph of Compound I having Form A is further characterized by having x-ray powder diffraction pattern peak positions at degree two-theta of 14.5±0.3 and 18.1±0.3.

5. The method of claim 4, wherein the crystalline polymorph of Compound I having Form A is further characterized by having x-ray powder diffraction pattern peak positions at degree two-theta of 9.7±0.3 and 21.2±0.3.

6. The method of claim 5, wherein the crystalline polymorph of Compound I having Form A is further characterized by having x-ray powder diffraction pattern peak positions at degree two-theta of 14.5±0.3, 18.1±0.3, 9.7±0.3, and 21.2±0.3.

7. The method of claim 3, wherein the crystalline polymorph of Compound I having Form A exhibits an x-ray powder diffraction pattern that is substantially similar to that of FIG. 4.

8. The method of claim 3, wherein the crystalline polymorph of Compound I having Form A exhibits a Raman spectrum that is substantially similar to that of FIG. 5.

9. The method of claim 3, wherein the crystalline polymorph of Compound I having Form A exhibits a differential scanning calorimetry thermogram having an endotherm with an onset of about 244° C.

10. The method of claim 3, wherein the crystalline polymorph of Compound I having Form A exhibits a differential scanning calorimetry thermogram having an endotherm with a peak of about 250° C.

11. The method of claim 3, wherein the crystalline polymorph of Compound I having Form A exhibits an x-ray powder diffraction pattern having seven or more peak positions at degree two-theta selected from the group consisting of: 7.160, 8.757, 9.820, 10.161, 12.459, 14.641, 15.219, 17.680, 18.240, 19.104, 20.220, 21.381, 22.579, 23.721, 24.898, 25.761, 25.522, 27.161, 28.321, 29.481, 30.921, and 34.281.

12. The method of claim 1, the crystalline polymorph of Compound I having Form B.

13. The method of claim 12, wherein the crystalline polymorph of Compound I having Form B is characterized as having an x-ray powder diffraction pattern exhibiting three or more peak positions at a degree two-theta selected from the group consisting of about: 9.8±0.3, 10.2±0.3, 14.5±0.3, 17.8±0.3, 18.5±0.3, 19.6±0.3, 21.0±0.3, 21.7±0.3, and 23.1±0.3.

14. The method of claim 12, wherein the crystalline polymorph of Compound I having Form B exhibits an x-ray powder diffraction pattern that is substantially similar to that of FIG. 11.

15. The method of claim 12, wherein the crystalline polymorph of Compound I having Form B exhibits a differential scanning calorimetry thermogram comprising an exotherm with an onset of about 106° C.; and
    exhibits a differential scanning calorimetry thermogram comprising an exotherm with a peak of about 120° C.; and
    exhibits a differential scanning calorimetry thermogram comprising an endotherm with an onset of about 225° C.; and
    exhibits a differential scanning calorimetry thermogram comprising an endotherm with a peak of about 253° C.

Figure 13:
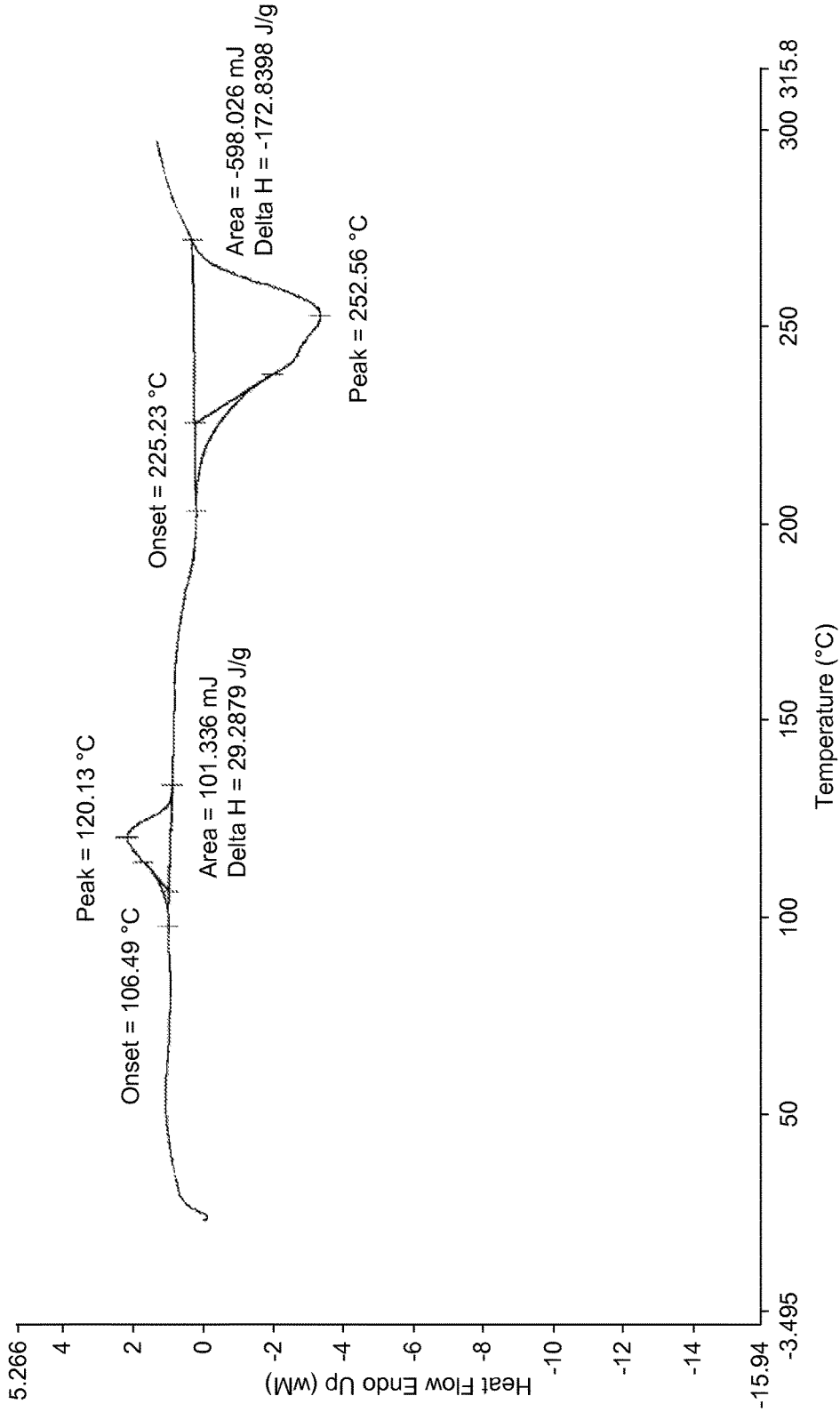
FIG. 13 is DSC spectra of the polymorphic form, Form B of Compound I.

16. The method of claim 12, wherein the crystalline polymorph of Compound I having Form B exhibits a differential scanning calorimetry thermogram that is substantially similar to FIG. 13.

17. The method of claim 1, the crystalline polymorph of Compound I having Form C.

18. The method of claim 17, wherein the crystalline polymorph of Compound I having Form C is characterized as having an x-ray powder diffraction pattern exhibiting three or more peak positions at a degree two-theta selected from the group consisting of about: 9.8±0.3, 10.2±0.3, 14.3±0.3, 17.4±0.3, 18.2±0.3, 18.9±0.3, 19.2±0.3, 22.1±0.3, 22.7±0.3, and 29.1±0.3.

19. The method of claim 17, wherein the crystalline polymorph of Compound I having Form C exhibits an x-ray powder diffraction pattern that is substantially similar to FIG. 14.

20. The method of claim 1, the crystalline polymorph of Compound I having Form D.

21. The method of claim 20, wherein the crystalline polymorph of Compound I having Form D is further characterized by having an x-ray powder diffraction pattern peak positions at a degree two-theta of about: 8.5±0.3, 14.9±0.3 and 17.0±0.3.

22. The method of claim 20, wherein the crystalline polymorph of Compound I having Form D exhibits an x-ray powder diffraction pattern substantially similar to that of FIG. 16.

23. The method of claim 1, the crystalline polymorph of Compound I having Form E.

24. The method of claim 23, wherein the crystalline polymorph of Compound I having Form E is further characterized by having an x-ray powder diffraction pattern peak positions at a degree two-theta of about: 5.6±0.3, 9.5±0.3 and 18.9±0.3.

25. The method of claim 23, wherein the crystalline polymorph of Compound I having Form E exhibits an x-ray powder diffraction pattern substantially the same as FIG. 17.

* * * * *